United States Patent
MacLachlan et al.

(10) Patent No.: US 7,982,027 B2
(45) Date of Patent: *Jul. 19, 2011

(54) LIPID ENCAPSULATED INTERFERING RNA

(75) Inventors: Ian MacLachlan, Vancouver (CA); Ellen Grace Ambegia, Vancouver (CA); James Heyes, Vancouver (CA)

(73) Assignee: Protiva Biotherapeutics, Inc., Burnaby, B.C. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/426,907

(22) Filed: Jun. 27, 2006

(65) Prior Publication Data

US 2006/0240093 A1    Oct. 26, 2006

Related U.S. Application Data

(63) Continuation of application No. 10/893,121, filed on Jul. 16, 2004, now abandoned.

(60) Provisional application No. 60/529,406, filed on Dec. 11, 2003, provisional application No. 60/503,279, filed on Sep. 15, 2003, provisional application No. 60/488,144, filed on Jul. 16, 2003.

(51) Int. Cl.
    *C07H 21/04* (2006.01)
    *C12N 15/88* (2006.01)

(52) U.S. Cl. .................... 536/24.5; 435/458

(58) Field of Classification Search ........... 536/24.5; 435/458

See application file for complete search history.

(56) References Cited

U.S. PATENT DOCUMENTS

| | | | |
|---|---|---|---|
| 4,394,448 A | 7/1983 | Szoka, Jr. et al. | |
| 4,438,052 A | 3/1984 | Weder et al. | |
| 4,515,736 A | 5/1985 | Deamer | |
| 4,598,051 A | 7/1986 | Papahadjopoulos et al. | |
| 4,897,355 A | 1/1990 | Eppstein et al. | |
| 5,013,556 A | 5/1991 | Woodle et al. | |
| 5,171,678 A | 12/1992 | Behr et al. | |
| 5,208,036 A | 5/1993 | Eppstein et al. | |
| 5,225,212 A | 7/1993 | Martin et al. | |
| 5,264,618 A | 11/1993 | Felgner et al. | |
| 5,279,833 A | 1/1994 | Rose | |
| 5,283,185 A | 2/1994 | Epand et al. | |
| 5,320,906 A | 6/1994 | Eley et al. | |
| 5,545,412 A | 8/1996 | Eppstein et al. | |
| 5,578,475 A | 11/1996 | Jessee | |
| 5,641,662 A | 6/1997 | Debs et al. | |
| 5,656,743 A | 8/1997 | Busch et al. | |
| 5,703,055 A | 12/1997 | Felgner et al. | |
| 5,705,385 A | 1/1998 | Bally et al. | |
| 5,820,873 A | 10/1998 | Choi et al. | |
| 5,885,613 A | 3/1999 | Holland et al. | |
| 5,976,567 A | 11/1999 | Wheeler et al. | |
| 5,981,501 A | 11/1999 | Wheeler et al. | |
| 6,165,501 A | 12/2000 | Tirosh et al. | |
| 6,284,267 B1 | 9/2001 | Aneja | |
| 6,287,591 B1 | 9/2001 | Semple et al. | |
| 6,534,484 B1 | 3/2003 | Wheeler et al. | |
| 6,586,410 B1 | 7/2003 | Wheeler et al. | |
| 6,649,780 B1 | 11/2003 | Eibl et al. | |
| 6,696,424 B1 | 2/2004 | Wheeler | |
| 6,815,432 B2 | 11/2004 | Wheeler et al. | |
| 6,858,224 B2 | 2/2005 | Wheeler et al. | |
| 7,422,902 B1 * | 9/2008 | Wheeler et al. | 435/458 |
| 7,803,397 B2 | 9/2010 | Heyes et al. | |
| 2001/0048940 A1 * | 12/2001 | Tousignant et al. | 424/450 |
| 2003/0077829 A1 * | 4/2003 | MacLachlan | 435/458 |
| 2003/0143732 A1 * | 7/2003 | Fosnaugh et al. | 435/325 |
| 2004/0063654 A1 | 4/2004 | Davis et al. | |
| 2004/0142892 A1 | 7/2004 | Finn et al. | |
| 2004/0253723 A1 | 12/2004 | Tachas et al. | |
| 2004/0259247 A1 * | 12/2004 | Tuschl et al. | 435/375 |
| 2005/0064595 A1 | 3/2005 | MacLachlan et al. | |
| 2005/0118253 A1 * | 6/2005 | MacLachlan et al. | 424/450 |

FOREIGN PATENT DOCUMENTS

| | | |
|---|---|---|
| CA | 2309727 A1 | 4/1999 |
| CA | 2271582 A1 | 11/1999 |
| CA | 2330741 A1 | 11/1999 |
| CA | 2397016 A1 | 7/2001 |
| JP | 03-126211 | 5/1991 |
| JP | 05-202085 | 8/1993 |
| JP | 06080560 | 3/1994 |
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |
| WO | WO 96/02655 A1 | 2/1996 |
| WO | WO 96/10390 A1 | 4/1996 |
| WO | WO 96/41873 A1 | 12/1996 |
| WO | WO 98/51285 A2 | 11/1998 |
| WO | WO 00/03683 A2 | 1/2000 |
| WO | WO 00/15820 A1 | 3/2000 |

(Continued)

OTHER PUBLICATIONS

Brummelkamp et al. (2002) Science 296:550-553.*
Wheeler et al. (1999) Gene Therapy 6:271-281.*
Liu et al. (1995) "Cationic liposome-mediated intravenous gene delivery" J. Biol. Chem. 270:24864-24870.*
Sorensen et al. (2003) "Gene Silencing by Systemic Delivery of Synthetic siRNAs in Adult Mice" J Mol Biol. Apr. 4;327(4):761-6.*
Templeton (2002) "Cationic Liposome-mediated Gene Delivery In vivo" Bioscience Reports, vol. 22, No. 2, pp. 283-295.*
Bass (2001) Nature 411:428-9.*
Lawrence et al. "The formation, characterization and stability of non-ionic surfactant vesicles," S.T.P. Pharma Sciences, 1996, vol. 6, No. 1, pp. 49-60.

(Continued)

*Primary Examiner* — Brian Whiteman
(74) *Attorney, Agent, or Firm* — Kilpatrick Townsend & Stockton LLP

(57) ABSTRACT

The present invention provides compositions and methods for silencing gene expression by delivering nucleic acid-lipid particles comprising a siRNA molecule to a cell.

63 Claims, 22 Drawing Sheets

FOREIGN PATENT DOCUMENTS

| WO | WO 00/62813 A2 | 10/2000 |
|---|---|---|
| WO | WO/01/05374 * | 1/2001 |
| WO | WO 01/05873 A1 | 1/2001 |
| WO | WO/02/34236 * | 2/2002 |
| WO | WO 02/087541 A1 | 11/2002 |
| WO | WO 03/097805 A2 | 11/2003 |
| WO | WO 2004/065546 A2 | 8/2004 |
| WO | WO 2004/110499 A1 | 12/2004 |
| WO | WO 2005/007196 A2 | 1/2005 |
| WO | WO 2005/026372 A1 | 3/2005 |
| WO | WO 2005/120152 A2 | 12/2005 |

OTHER PUBLICATIONS

Shin, et al. "Acid-triggered release via dePEGylation of DOPE liposomes containing acid-labile vinyl ether PEG-lipids," Journal of Controlled Release, 2003, vol. 91, pp. 187-200.

Chonn et al., "Recent advances in liposomal drug-delivery systems," Current Opinion in Biotechnology, 1995, pp. 698-708, vol. 6.

Heyes et al., "Cationic lipid saturation influences intracellular delivery of encapsulated nucleic acids," Journal of Controlled Release, 2005, vol. 107, pp. 276-287.

Heyes et al., "Synthesis of novel cationic lipids: effect of structural modification on the efficiency of gene transfer," J. Med. Chem., 2002, vol. 45, pp. 99-114.

Lawrence et al., "Synthesis and aggregation properties of dialkyl polyoxyethylene glycerol ethers," Chemistry and Physics of Lipids, 1996, 82(2):89-100.

Murahashi et al., "Synthesis and evaluation of neoglycolipid for liposome modification," Biol. Pharm. Bull., 1997, 20(6):704-707.

Parr et al., Factors influencing the retention and chemical stability of polly(ethylene glycol)-lipid conjugates incorporated into large unilamellar vesicles, Biochimica et Biophysica Acta, 1994, 1195:21-30.

Sawada et al., "Microemulsions in supercritical $CO_2$ utilizing the polyethyleneglycol dialkylglycerol and their use for the solubilization of hydrophiles," Dyes and Pigments, 2005, pp. 64-74, vol. 65.

Song et al., "Characterization of the inhibitory effect of PEG-lipid conjugates on the intracellular delivery of plasmid and antisense DNA mediated by cationic lipid liposomes," Biochimica et Biophysica Acta, 2002, 1558:1-13.

JP06080560—English abstract from CAplus.

Arpicco, S., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco, S., et al., "Synthesis, characterization and transfection activity of new saturated and unsaturated cationic lipids," IL Farmaco, 2004, vol. 59, pp. 869-878.

Ballas, N., et al., "Liposomes bearing a quaternary ammonium detergent as an efficient vehicle for functional transfer of TMV-RNA into plant protoplasts," Biochimica et Biophysica Acta, 1988, vol. 939, pp. 8-18.

Barinaga, M., "Step Taken Toward Improved Vectors for Gene Transfer," Science, 1994, vol. 266, p. 1326.

Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

Behr, J.-P., "Synthetic Gene-Transfer Vectors," Acc. Chem. Res., 1993, vol. 26, pp. 274-278.

Brigham, K., et al., "Rapid Communication: In vivo Transfection of Murine Lungs with Functioning Prokaryotic Gene Using a Liposome Vehicle," The American Journal of the Medical Sciences, vol. 298, No. 4, pp. 278-281, 1989.

Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.

Cortesi, R., et al., "Effect of cationic liposome composition on in vitro cytotoxicity and protective effect on carried DNA," International Journal of Pharmaceutics, 1996, vol. 139, pp. 69-78.

Crystal, R., "Transfer of Genes to Humans: Early Lessons and Obstacles to Success," Science, 1995, vol. 270, pp. 404-410.

Culver K., "The First Human Gene Therapy Experiment," Gene Therapy: A Handbook for Physicians, 1994, pp. 33-40.

Duzgunes, N., "Membrane Fusion," Subcellular Biochemistry, 1985, vol. 11, pp. 195-286.

Dwarki, V.J., et al., "Cationic Liposome-Mediated RNA Transfection," Methods in Enzymology, 1993, vol. 217, pp. 644-654.

Enoch, H., et al., "Formation and properties of 1000-Å-diameter, single-bilayer phospholipid vesicles," Proc. Natl. Acad. Sci. USA, 1979, vol. 76, No. 1, pp. 145-149.

Felgner, J., et al., "Cationic Lipid-Mediated Transfection in Mammalian Cells: 'Lipofection,'" J. Tiss. Cult. Meth., 1993, vol. 15, pp. 63-68.

Felgner, J., et al., "Enhanced Gene Delivery and Mechanism Studies with a Novel Series of Cationic Lipid Formulations," The Journal of Biological Chemistry, 1994, vol. 269, No. 4, pp. 2550-2561.

Felgner, P., et al., "Lipofection: A highly efficient, lipid-mediated DNA-transfection procedure," Proc. Natl. Acad. Sci. USA, 1987, vol. 84, pp. 7413-7417.

Felgner, P.L., et al., "Cationic Liposome Mediated Transfection," Proc. West. Pharmacol. Soc., 1989, vol. 32, pp. 115-121.

Gao, X., et al., "A Novel Cationic Liposome Reagent for Efficient Transfection of Mammalian Cells," Biochem. Biophys. Res. Comm., 1991, vol. 179, No. 1, pp. 280-285.

Gershon, H., et al., "Mode of Formation and Structural Feature of DNA-Cationic Liposome Complexes Used for Transfection," Biochemistry, 1993, vol. 32, pp. 7143-7151.

Guy-Caffey, J., et al., "Novel Polyaminolipids Enhance the Cellular Uptake of Oligonucleotides," The Journal of Biological Chemistry, 1995, vol. 270, No. 52, pp. 31391-31396.

Hawley-Nelson, P., et al., "LipofectAmine™ Reagent: A New, Higher Efficiency Polycationic Liposome Transfection Reagent," Focus, 1993, vol. 15, No. 3, pp. 73-80.

Hyde, S., et al., "Correction of the ion transport defect in cystic fibrosis transgenic mice by gene therapy," Nature, 1993, vol. 362, pp. 250-255.

Jiang, L., et al., "Comparison of protein precipitation methods for sample preparation prior to proteomic analysis," Journal of Chromatography A, 2004, vol. 1023, pp. 317-320.

Juliano, R., et al., "The Effect of Particle Size and Charge on the Clearance Rates of Liposomes and Liposome Encapsulated Drugs," Biochem. Biophys. Res. Commun., 1975, vol. 63, No. 3, pp. 651-658.

Keough, K., "Influence of chain unsaturation and chain position on thermotropism and intermolecular interactions in membranes," Biochem. Soc. Transactions, 1990, vol. 18, No. 5, pp. 835-837.

Legendre, J.-Y. et al., "Delivery of Plasmid DNA into Mammalian Cell Lines Using pH-Sensitive Liposomes: Comparison with Cationic Liposomes," Pharm. Res., 1992, vol. 9, No. 10, pp. 1235-1242.

Leventis, R., et al., "Interactions of mammalian cells with lipid dispersions containing novel metabolizable cationic amphiphiles," Biochem. Biophys. Acta, 1990, vol. 1023, pp. 124-132.

Marshall, E., "Gene Therapy's Growing Pains," Science, 1995, vol. 269, pp. 1050-1055.

Orkin, S., et al., NIH Report, Report and Recommendations of the Panel to Assess the NIH Investment in Research on Gene Therapy, 1995.

Paul, C., et al., "Effective expression of small interfering RNA in human cells," Nature Biotech., 2002, vol. 20, pp. 505-508.

Puyal, C., et al., "A new cationic liposome encapsulating genetic material: A potential delivery system for polynucleotides," Eur. J. Biochem., 1995, vol. 228, pp. 697-703.

Spagnou, S., et al., "Lipidic Carriers of siRNA: Differences in the Formulation, Cellular Uptake, and Delivery with Plasmid DNA," Biochemistry, 2004, vol. 43, pp. 13348-13356.

Stamatatos, L., et al., "Interactions of Cationic Lipid Vesicles with Negatively Charged Phospholipid Vesicles and Biological Membranes," Biochemistry, 1988, vol. 27, pp. 3917-3925.

Szoka, F., et al., "Comparative Properties and Methods of Preparation of Lipid Vesicles (Liposomes)," Ann. Rev. Biophys. Bioeng., 1980, vol. 9, pp. 467-508.

Szoka, F., et al., "Procedure for preparation of liposomes with large internal aqueous space and high capture by reverse-phase evaporation," Proc. Natl. Acad. Sci. USA, 1978, vol. 75, No. 9, pp. 4194-4198.

Van Der Woude, I., et al., "Parameters influencing the introduction of plasmid DNA into cells by the use of synthetic amphiphiles as a carrier system," Biochimica et Biophysica Acta, 1995, vol. 1240, pp. 34-40.

Wilson, R., et al., "Counterion-Induced Condensation of Deoxyribonucleic Acid. A Light-Scattering Study," Biochemistry, 1979, vol. 18, No. 11, pp. 2192-2196.

Woodle, M.C., et al., "Versatility in lipid compositions showing prolonged circulation with sterically stabilized liposomes," Biochimica et Biophysica Acta, 1992, vol. 1105, pp. 193-200.

Zhu, N., et al., "Systemic Gene Expression After Intravenous DNA Delivery into Adult Mice," Science, 1993, vol. 261, pp. 209-211.

* cited by examiner a) Figure 6A: Liver DNA Concentration Profile in Neuro-2a Tumour Bearing Male A/J Mice Following a Single Intravenous Administration of SPLP Containing PEG-Diacylglycerol

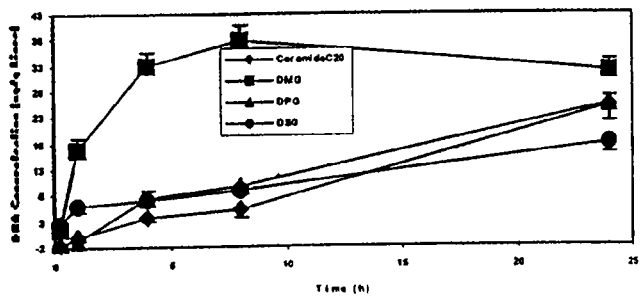

b) Figure 6B: Spleen DNA Concentration Profile in Neuro-2a Tumour Bearing Male A/J Mice Following a Single Intravenous Administration of SPLP Containing PEG-Diacylglycerol

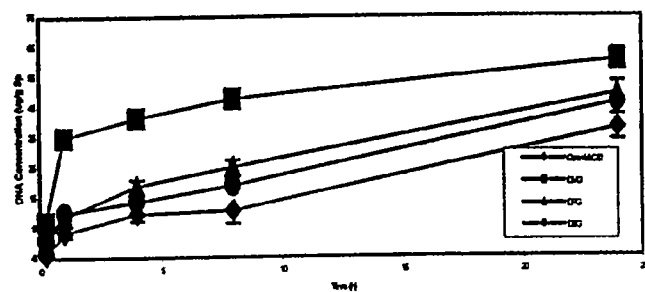

c) Figure 6C: Lung DNA Concentration Profile in Neuro-2a Tumour Bearing Male A/J Mice Following a Single Intravenous Administration of SPLP Containing PEG-Diacylglycerol

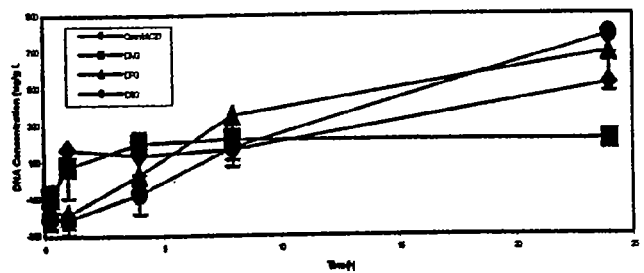

d) Figure 6D: Neuro-2a Tumor DNA Concentration Profile in Male A/J Mice Following a Single Intravenous Administration of SPLP Containing PEG-Diacylglycerol

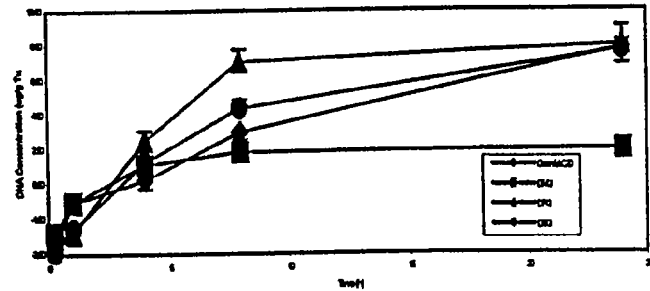

Figure 6

*N*-(2,3-dimyristyloxypropyl) amide PEG$_{2000}$ methyl ether (PEG-A-DMA)
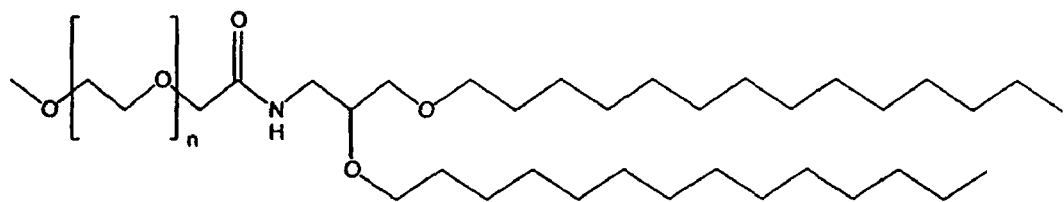
*N*-(2,3-dimyristyloxypropyl) carbamate PEG$_{2000}$ methyl ether (PEG-C-DMA)
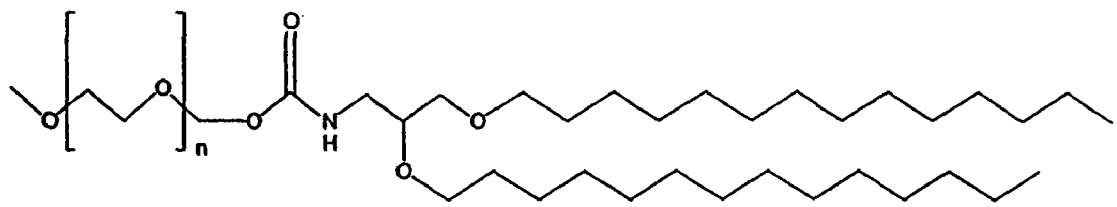
N-(2,3-dimyristyloxypropyl) succinamide PEG$_{2000}$ methyl ether (PEG-S-DMA)
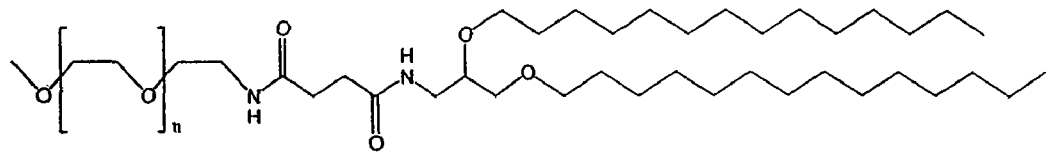
Figure 10

LIPID ENCAPSULATED INTERFERING RNA

CROSS-REFERENCES TO RELATED APPLICATIONS

This application claims the benefit of U.S. Provisional Patent Application No. 60/529,406, filed Dec. 11, 2003; 60/503,279, filed Sep. 15, 2003, and 60/488,144, filed Jul. 16, 2003, the disclosures of each of which are hereby incorporated by reference in their entirety for all purposes.

FIELD OF THE INVENTION

The present invention relates to compositions and methods for the therapeutic delivery of a nucleic acid by delivering a serum-stable lipid delivery vehicle encapsulating the nucleic acid to provide efficient RNA interference (RNAi) in a cell or mammal. More particularly, the present invention is directed to using a small interfering RNA (siRNA) encapsulated in a serum-stable lipid particle having a small diameter suitable for systemic delivery.

BACKGROUND OF THE INVENTION

RNA interference (RNAi) is an evolutionarily conserved, sequence specific mechanism triggered by double stranded RNA (dsRNA) that induces degradation of complementary target single stranded mRNA and "silencing" of the corresponding translated sequences (McManus and Sharp, *Nature Rev. Genet.* 3:737 (2002)). RNAi functions by enzymatic cleavage of longer dsRNA strands into biologically active "short-interfering RNA" (siRNA) sequences of about 21-23 nucleotides in length (Elbashir, et al., Genes Dev. 15:188 (2001)). siRNA can be used downregulate or silence the translation of a gene product of interest. For example, it is desirable to downregulate genes associated with various diseases and disorders.

Delivery of siRNA remains problematic (see, e.g., Novina and Sharp, *Nature* 430::161-163 (2004); and Garber, *J. Natl. Cancer Inst.* 95(7):500-2 (2003)). An effective and safe nucleic acid delivery system is required for siRNA to be therapeutically useful. Naked dsRNA administered to most subjects will: (1) be degraded by endogenous nucleases; and (2) will not be able to cross cell membranes to contact and silence their target gene sequences.

Viral vectors are relatively efficient gene delivery systems, but suffer from a variety of safety concerns, such as potential for undesired immune responses. Furthermore, viral systems are rapidly cleared from the circulation, limiting transfection to "first-pass" organs such as the lungs, liver, and spleen. In addition, these systems induce immune responses that compromise delivery with subsequent injections. As a result, non-viral gene delivery systems are receiving increasing attention (Worgall, et al., *Human Gene Therapy* 8:37 (1997); Peeters, et al., Human Gene Therapy 7:1693 (1996); Yei, et al., *Gene Therapy* 1: 192 (1994); Hope, et al., *Molecular Membrane Biology* 15:1 (1998)).

Plasmid DNA-cationic liposome complexes are currently the most commonly employed nonviral gene delivery vehicles (Felgner, Scientific American 276:102 (1997); Chonn, et al., *Current Opinion in Biotechnology* 6:698 (1995)). For instance, cationic liposome complexes made of an amphipathic compound, a neutral lipid, and a detergent for transfecting insect cells are disclosed in U.S. Pat. No. 6,458,382. Cationic liposome complexes are also disclosed in U.S. Patent Application Publication No. 2003/0073640. Cationic liposome complexes, however, are large, poorly defined systems that are not suited for systemic applications and can elicit considerable toxic side effects (Harrison, et al., *Biotechniques* 19:816 (1995); Li, et al., *The Gene* 4:891 (1997); Tam, et al, *Gene Ther.* 7:1867 (2000)). As large, positively charged aggregates, lipoplexes are rapidly cleared when administered in vivo, with highest expression levels observed in first-pass organs, particularly the lungs (Huang, et al., *Nature Biotechnology* 15:620 (1997); Templeton, et al., *Nature Biotechnology* 15:647 (1997); Hofland, et al., *Pharmaceutical Research* 14:742 (1997)).

Other liposomal delivery systems include, for example, the use of reverse micelles, anionic and polymer liposomes as disclosed in, e.g., U.S. Pat. No. 6,429,200; U.S. Patent Application No. 2003/0026831; and U.S. Patent Application Nos. 2002/0081736 and 2003/0082103, respectively.

Recent work has shown that nucleic acids can be encapsulated in small (about 70 nm diameter) "stabilized plasmid-lipid particles" (SPLP) that consist of a single plasmid encapsulated within a bilayer lipid vesicle (Wheeler, et al., *Gene Therapy* 6:271 (1999)). These SPLPs typically contain the "fusogenic" lipid dioleoylphosphatidylethanolamine (DOPE), low levels of cationic lipid (i.e., 10% or less), and are stabilized in aqueous media by the presence of a poly(ethylene glycol) (PEG) coating. SPLP have systemic application as they exhibit extended circulation lifetimes following intravenous (i.v.) injection, accumulate preferentially at distal tumor sites due to the enhanced vascular permeability in such regions, and can mediate transgene expression at these tumor sites. The levels of transgene expression observed at the tumor site following i.v. injection of SPLP containing the luciferase marker gene are superior to the levels that can be achieved employing plasmid DNA-cationic liposome complexes (lipoplexes) or naked DNA.

However, there remains a strong need in the art for novel and more efficient methods and compositions for introducing nucleic acids, such as siRNA, into cells. The present invention addresses this and other needs.

BRIEF SUMMARY OF THE INVENTION

The present invention provides stable nucleic acid-lipid particles (SNALP) useful for encapsulating one or more siRNA molecules, methods of making SNALPs comprising siRNA, SNALPs comprising siRNA and methods of delivering and/or administering the SNALPs to a subject to silence expression of a target gene sequence.

In one embodiment, the invention provide nucleic acid-lipid particles comprising: a cationic lipid, a non-cationic lipid, a conjugated lipid that inhibits aggregation of particles and a siRNA. In some embodiments, the siRNA molecule is fully encapsulated within the lipid bilayer of the nucleic acid-lipid particle such that the nucleic acid in the nucleic acid-lipid particle is resistant in aqueous solution to degradation by a nuclease. The nucleic acid particle are substantially non-toxic to mammals. The siRNA molecule may comprise about 15 to about 60 nucleotides. The siRNA molecule may be derived from a double-stranded RNA greater than about 25 nucleotides in length. In some embodiments the siRNA is transcribed from a plasmid, in particular a plasmid comprising a DNA template of a target sequence.

The cationic lipid may be one or more of N,N-dioleyl-N,N-dimethylammonium chloride (DODAC), N,N-distearyl-N,N-dimethylammonium bromide (DDAB), N-(1-(2,3-dioleyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA), and a mixture thereof. The non-cationic lipid may be one or more of dioleoylphosphatidylethanolamine (DOPE), palmitoyloleoylphosphatidylcholine (POPC), egg phosphatidylcholine (EPC), distearoylphosphatidylcholine (DSPC), cholesterol, and combinations thereof.

The conjugated lipid that inhibits aggregation of particles may be one or more of a polyethyleneglycol (PEG)-lipid conjugate, a polyamide (ATTA)-lipid conjugate, and combinations thereof. The PEG-lipid conjugate may be one or more of a PEG-dialkyloxypropyl (DAA), a PEG-diacylglycerol (DAG), a PEG-phospholipid, a PEG-ceramide, and combinations thereof. The PEG-DAG conjugate may be one or more of a PEG-dilauroylglycerol ($C_{12}$), a PEG-dimyristoylglycerol ($C_{14}$), a PEG-dipalmitoylglycerol ($C_{16}$), and a PEG-distearoylglycerol ($C_{18}$), and combinations thereof. The PEG-DAA conjugate may be one or more of a PEG-dilauryloxypropyl ($C_{12}$), a PEG-dimyristyloxypropyl ($C_{14}$), a PEG-dipalmityloxypropyl ($C_{16}$), and a PEG-distearyloxypropyl ($C_{18}$), and combinations thereof. The nucleic acid-lipid particle may further comprise a cationic polymer lipid.

In some embodiments, the particles are made by providing an aqueous solution in a first reservoir and an organic lipid solution in a second reservoir and mixing the aqueous solution with the organic lipid solution so as to substantially instantaneously produce a liposome encapsulating an interfering RNA. In some embodiments, the particles are made by formation of hydrophobic intermediate complexes in either detergent-based or organic solvent-based systems, followed by removal of the detergent or organic solvent. Preferred embodiments are charge-neutralized.

In one embodiment, the interfering RNA is transcribed from a plasmid and the plasmid is combined with cationic lipids in a detergent solution to provide a coated nucleic acid-lipid complex. The complex is then contacted with non-cationic lipids to provide a solution of detergent, a nucleic acid-lipid complex and non-cationic lipids, and the detergent is then removed to provide a solution of serum-stable nucleic acid-lipid particles, in which the plasmid comprising an interfering RNA template is encapsulated in a lipid bilayer. The particles thus formed have a size of about 50-150 nm.

In another embodiment, serum-stable nucleic acid-lipid particles are formed by preparing a mixture of cationic lipids and non-cationic lipids in an organic solvent; contacting an aqueous solution of nucleic acids comprising interfering RNA with the mixture of cationic and non-cationic lipids to provide a clear single phase; and removing the organic solvent to provide a suspension of nucleic acid-lipid particles, in which the nucleic acid is encapsulated in a lipid bilayer, and the particles are stable in serum and have a size of about 50-150 nm.

The nucleic acid-lipid particles of the present invention are useful for the therapeutic delivery of nucleic acids comprising a siRNA sequence. In particular, it is an object of this invention to provide in vitro and in vivo methods for treatment of a disease in a mammal by downregulating or silencing the translation of a target nucleic acid sequence. In these methods, a siRNA molecule is formulated into a nucleic acid-lipid particle, and the particles are administered to patients requiring such treatment (e.g., a patient diagnosed with a disease or disorder associated with the expression or overexpression of a gene comprising the target nucleic acid sequence). Alternatively, cells are removed from a patient, the siRNA is delivered in vitro, and the cells are reinjected into the patient. In one embodiment, the present invention provides for a method of introducing a siRNA molecule into a cell by contacting a cell with a nucleic acid-lipid particle comprising of a cationic lipid, a non-cationic lipid, a conjugated lipid that inhibits aggregation, and a siRNA.

The nucleic acid-lipid particle may be administered, e.g., intravenously, parenterally or intraperitoneally. In one embodiment, at least about 10% of the total administered dose of the nucleic acid-lipid particles is present in plasma about 24, 36, 48, 60, 72, 84, or 96 hours after injection. In other embodiments, more than 20%, 30%, 40% and as much as 60%, 70% or 80% of the total injected dose of the nucleic acid-lipid particles is present in plasma 24, 36, 48, 60, 72, 84, or 96 hours after injection. In one embodiment, the presence of a siRNA in cells in a target tissue (i.e., lung, liver, tumor or at a site of inflammation) is detectable at 24, 48, 72 and 96 hours after administration. In one embodiment, downregulation of expression of the target sequence is detectable at 24, 48, 72 and 96 hours after administration. In one embodiment, downregulation of expression of the target sequence occurs preferentially in tumor cells or in cells at a site of inflammation. In one embodiment, the presence of a siRNA in cells at a site distal to the site of administration is detectable at least four days after intravenous injection of the nucleic acid-lipid particle. In another embodiment, the presence of a siRNA in of cells in t a target tissue (i.e., lung, liver, tumor or at a site of inflammation) is detectable at least four days after injection of the nucleic acid-lipid particle.

The particles are suitable for use in intravenous nucleic acid transfer as they are stable in circulation, of a size required for pharmacodynamic behavior resulting in access to extravascular sites and target cell populations. The invention also provides for pharmaceutically acceptable compositions comprising a nucleic acid-lipid particle.

Another embodiment of the present invention provides methods for in vivo delivery of siRNA. A nucleic acid-lipid particle comprising a cationic lipid, a non-cationic lipid, a conjugated lipid that inhibits aggregation of particles, and siRNA is administered (e.g., intravenously, subcutaneously, intraperitoneally, or subdermally) to a subject (e.g., a mammal such as a human). In some embodiments, the invention provides methods for in vivo delivery of interfering RNA to the liver of a mammalian subject.

A further embodiment of the present invention provides a method of treating a disease or disorder in a mammalian subject. A therapeutically effective amount of a nucleic acid-lipid particle comprising a cationic lipid, a non-cationic lipid, a conjugated lipid that inhibits aggregation of particles, and siRNA is administered to the mammalian subject (e.g., a rodent such as a mouse, a primate such as a human or a monkey) with the disease or disorder. In some embodiments, the disease or disorder is associated with expression and/or overexpression of a gene and expression or overexpression of the gene is silenced by the siRNA. In some embodiments, the disease is a viral disease such as, for example, hepatitis (e.g., Hepatitis A, Hepatitis B, Hepatitis C, Hepatitis D, Hepatitis E, Hepatitis G, or a combination thereof). In some embodiment, the disease or disorder is a liver disease or disorder, such as, for example, dyslipidemia.

BRIEF DESCRIPTION OF THE DRAWINGS

FIG. 6 illustrates the biodistribution properties of SNALPs containing PEG-DAGs.

FIG. 10 illustrates the structures of three exemplary PEG-dialkyloxypropyl derivatives suitable for use in the present invention, i.e., N-(2,3-dimyristyloxypropyl) carbamate PEG$_{2000}$ methyl ether (i.e., PEG-C-DMA), N-(2,3-dimyristyloxypropyl)amide PEG$_{2000}$ methyl ether (i.e., PEG-A-DMA), and N-(2,3-dimyristyloxypropyl) succinamide PEG$_{2000}$ methyl ether (i.e., PEG-S-DMA).

DETAILED DESCRIPTION OF THE INVENTION

I. Introduction

Figure 1:
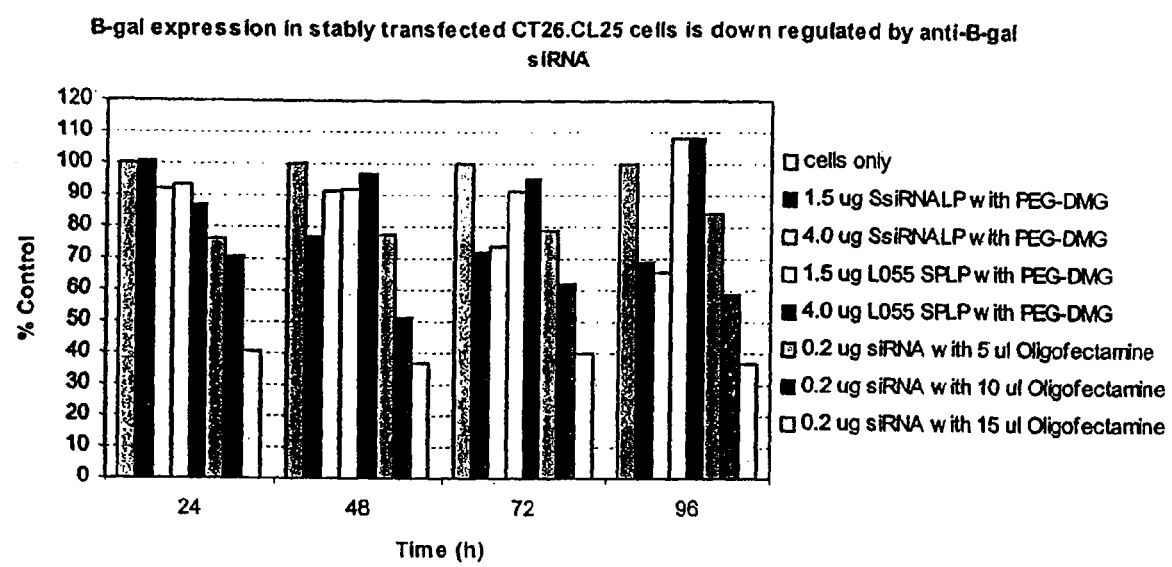
FIG. 1 illustrates downregulating 13-galactosidase expression in CT26.CL25 cells via in vitro delivery of encapsulated anti-β-galactosidase siRNA in DSPC:Cholesterol:DODMA:PEG-DMG liposomes.
Figure 2:
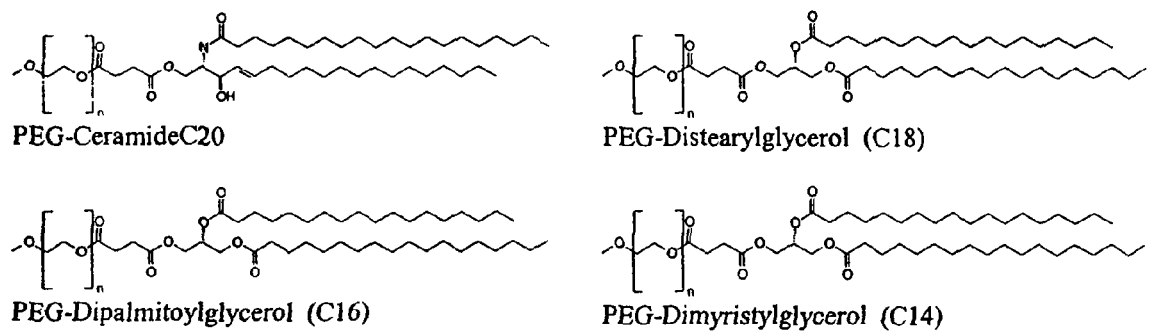
FIG. 2 illustrates the structures of PEG-Diacylglycerols and PEG-Ceramide $C_{20}$.
Figure 3:
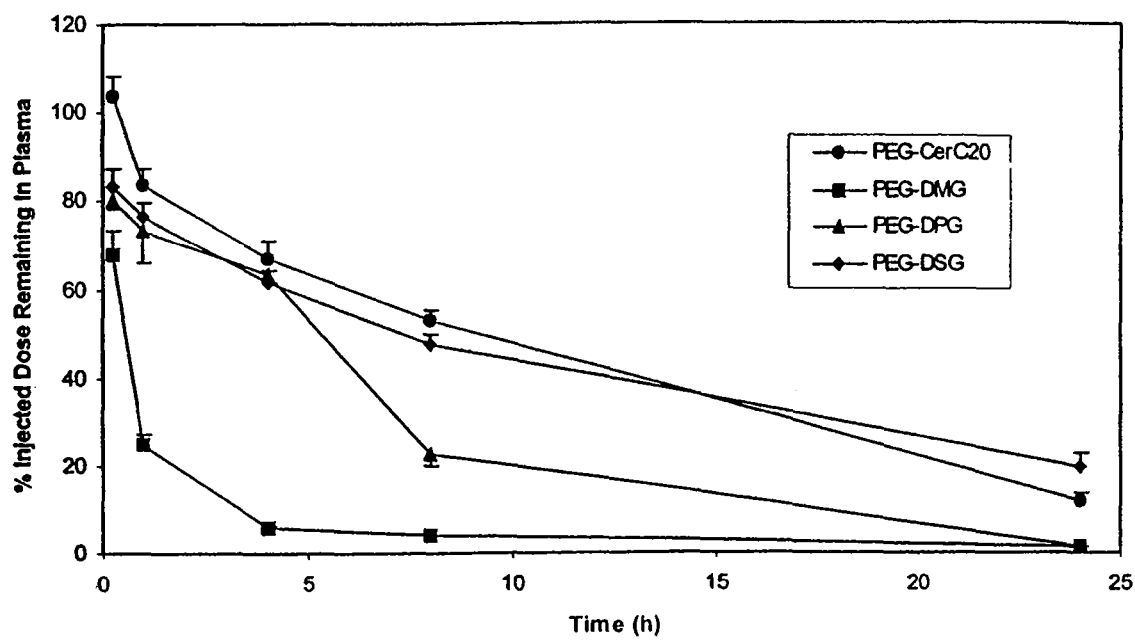
FIG. 3 illustrates that clearance studies with LUVs showed that SNALPs containing PEG-DAGs were comparable to SNALPs containing PEG-CeramideC20.
Figure 4:
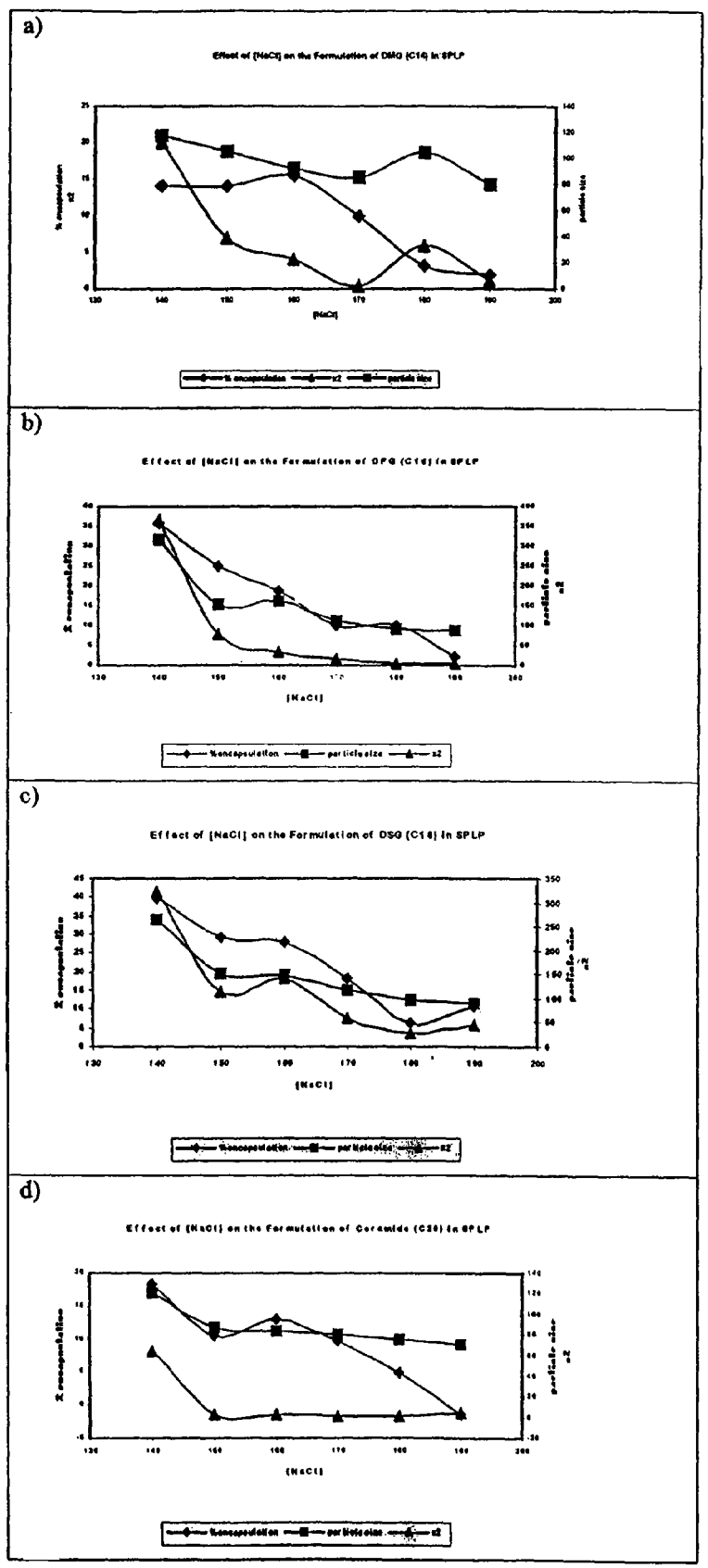
FIG. 4 illustrates that SNALPs containing PEG-DAGs can be formulated via a detergent dialysis method.
Figure 5:
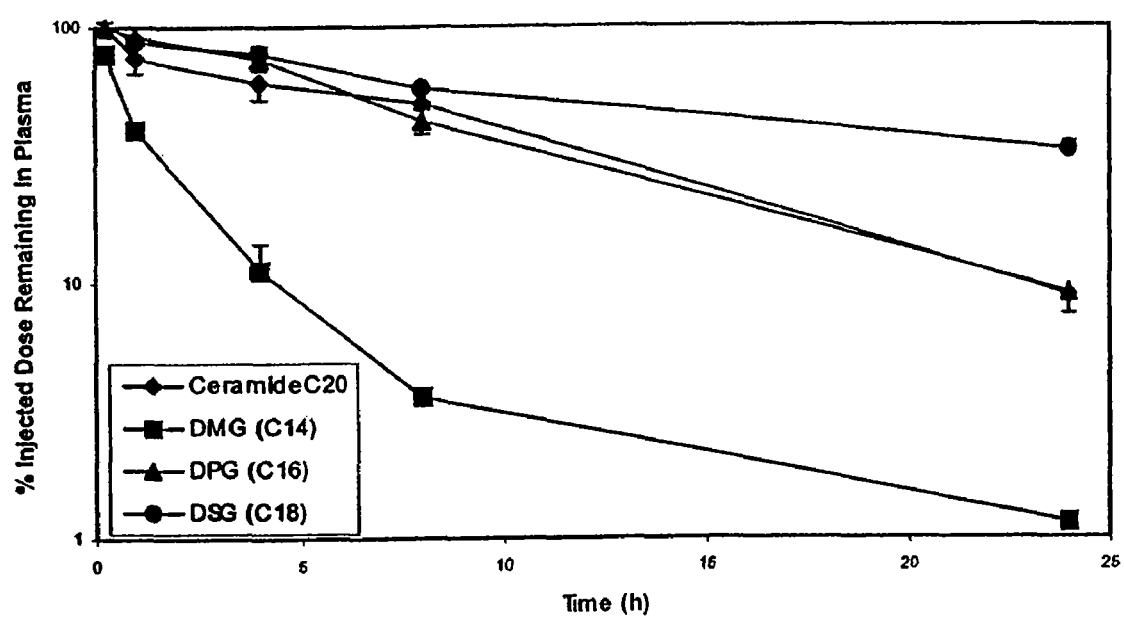
FIG. 5 illustrates the pharmacokinetic properties of SNALPs containing PEG-DAGs.

The present invention provides stable nucleic acid-lipid particles (SNALP) useful for encapsulating one or more siRNA molecules, methods of making SNALPs comprising siRNA, SNALPs comprising siRNA and methods of delivering and/or administering the SNALPs to a subject to silence expression of a target gene sequence.

The present invention is based on the unexpected success of encapsulating short interfering RNA (siRNA) molecules in SNALPs. Using the methods of the present invention, siRNA molecules are encapsulated in SNALPs with an efficiency greater than 70%, more usually with an efficiency greater than 80 to 90%. The SNALPs described herein can conveniently be used in vitro and in vivo to efficiently deliver administer siRNA molecules locally or systemically to cells expressing a target gene. Once delivered, the siRNA molecules in the SNALPs silence expression of the target gene.

The SNALPs described herein are typically <150 nm diameter and remain intact in the circulation for an extended period of time in order to achieve delivery of siRNA to target tissues. The SNALPs are highly stable, serum-resistant nucleic acid-containing particles that does not interact with cells and other components of the vascular compartment. Moreover, the SNALPs also readily interact with target cells at a disease site in order to facilitate intracellular delivery of a desired nucleic acid (e.g., a siRNA or a plasmid encoding a siRNA).

II. Definitions

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture.

As used herein, "lipid encapsulated" can refer to a lipid formulation that provides a compound with full encapsulation, partial encapsulation, or both. In a preferred embodiment, the nucleic acid is fully encapsulated in the lipid formulation.

As used herein, the term "SNALP" refers to a stable nucleic acid lipid particle. A SNALP represents a vesicle of lipids coating a reduced aqueous interior comprising a nucleic acid such as an interfering RNA sequence or a plasmid from which an interfering RNA is transcribed.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the inferior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of the SNALPs, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, and PEG conjugated to ceramides (see, U.S. Pat. No. 5,885,613, which is incorporated herein by reference).

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and .beta.-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "noncationic lipid" refers to any neutral lipid as described above as well as anionic lipids.

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). The following lipids are cationic and have a positive charge at below physiological pH: DODAP, DODMA, DMDMA and the like.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N—N-dialkylamino, 1,2-diacyloxy-3-aminopropane and 1,2-dialkyl-3-aminopropane.

The term "fusogenic" refers to the ability of a liposome, an SNALP or other drug delivery system to fuse with membranes of a cell. The membranes can be either the plasma membrane or membranes surrounding organelles, e.g., endosome, nucleus, etc.

The term "diacylglycerol" refers to a compound having 2-fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Diacylglycerols have the following general formula:

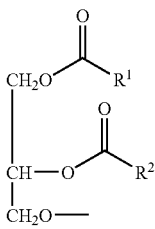

The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

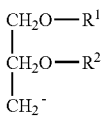

The term "ATTA" or "polyamide" refers to, but is not limited to, compounds disclosed in U.S. Pat. Nos. 6,320,017 and 6,586,559, both of which are incorporated herein by reference. These compounds include a compound having the formula

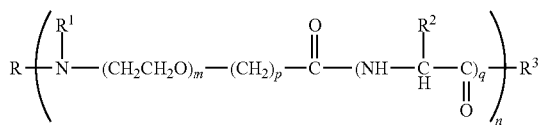

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "nucleic acid" or "polynucleotide" refers to a polymer containing at least two deoxyribonucleotides or ribonucleotides in either single- or double-stranded form. Unless specifically limited, the terms encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. The term nucleic acid is used interchangeably with gene, cDNA, mRNA encoded by a gene, and an interfering RNA molecule.

The term "gene" refers to a nucleic acid (e.g., DNA or RNA) sequence that comprises partial length or entire length coding sequences necessary for the production of a polypeptide or a polypeptide precursor (e.g., polypeptides or polypeptide preursors from hepatitis virus A, B, C, D, E, or G; or herpes simplex virus).

"Gene product," as used herein, refers to a product of a gene such as an RNA transcript, including, e.g., mRNA.

The term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA typically has substantial or complete identity to the target gene. The sequence of the interfering RNA can correspond to the full length target gene, or a subsequence thereof. Interfering RNA includes small-interfering RNA" or "siRNA," i.e., interfering RNA of about 15-60, 15-50, 15-50, or 15-40 (duplex) nucleotides in length, more typically about, 15-30, 15-25 or 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or maybe encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E coli* RNase III or Dicer. These enzymes process the dsRNA into biologically active siRNA (see, e.g., Yang et al., *PNAS USA* 99: 9942-7 (2002); Calegari et al., *PNAS USA* 99: 14236 (2002); Byrom et al., *Ambion TechNotes* 10(1): 4-6 (2003); Kawasaki et al., *Nucleic Acids Res.* 31: 981-7 (2003); Knight and Bass, *Science* 293: 2269-71 (2001); and Robertson et al., *J. Biol. Chem.* 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36 C is typical for low stringency amplification, although annealing temperatures may vary between about 32 C and 48 C depending on primer length. For high stringency PCR amplification, a temperature of about 62 C is typical, although high stringency annealing temperatures can range from about 50 C to about 65 C, depending on the primer length and specificity. Typical cycle conditions for both high and low stringency amplifications include a denaturation phase of 90 C-95 C for 30 sec-2 min., an annealing phase lasting 30 sec.-2 min., and an extension phase of about 72 C for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The terms "substantially identical" or "substantial identity," in the context of two or more nucleic acids, refer to two or more sequences or subsequences that are the same or have a specified percentage of nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "inhibiting expression of a target gene" refers to the ability of a siRNA of the invention to initiate gene silencing of the target gene. To examine the extent of gene silencing, samples or assays of the organism of interest or cells in culture expressing a particular construct are compared to control samples lacking expression of the construct. Control samples (lacking construct expression) are assigned a relative value of 100%. Inhibition of expression of a target gene is achieved when the test value relative to the control is about 90%, preferably 50%, more preferably 25-0%. Suitable assays include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

By "silencing" or "downregulation" of a gene or nucleic acid is intended to mean a detectable decrease of translation of a target nucleic acid sequence, i.e., the sequence targeted by the RNAi, or a decrease in the amount or activity of the target sequence or protein, in comparison to the level that is detected in the absence of the interfering RNA or other nucleic acid sequence. A detectable decrease can be as small as about 5% or 10%, or as great as about 80%, 90% or 100%. More typically, a detectable decrease is about 20%, 30%, 40%, 50%, 60%, or 70%.

A "therapeutically effective amount" or an "effective amount" of a siRNA is an amount sufficient to produce the desired effect, e.g., a decrease in the expression of a target sequence in comparison to the normal expression level detected in the absence of the siRNA.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism. In some embodiments, distal site refers to a site physically separated from a disease site (e.g., the site of a tumor, the site of inflammation, or the site of an infection).

"Serum-stable" in relation to nucleic acid-lipid particles means that the particle is not significantly degraded after exposure to a serum or nuclease assay that would significantly degrade free DNA. Suitable assays include, for example, a standard serum assay or a DNAse assay such as those described in the Examples below.

"Systemic delivery," as used herein, refers to delivery that leads to a broad biodistribution of a compound within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, intraperitoneal, In a preferred embodiment, systemic delivery of nucleic acid-lipid particles is by intravenous delivery.

"Local delivery" as used herein refers to delivery of a compound directly to a target site within an organism. For example, a compound can be locally delivered by direct injection into a disease site such as a tumor or other target site such as a site of inflammation or a target organ such as the liver, heart, pancreas, kidney, and the like, III. Stable Nucleic Acid-Lipid Particles The stable nucleic acid-lipid particles (SNALPs) described herein typically comprise a nucleic acid (e.g., a siRNA sequence or a DNA sequence encoding a siRNA sequence), a cationic lipid, a noncationic lipid and a bilayer stabilizing component such as, e.g., a conjugated lipid that inhibits aggregation of the SNALPs. The SNALPs of the present invention have a mean diameter of less than about 150 nm and are substantially nontoxic. In addition, nucleic acids encapsulated in the SNALPs of the present invention are resistant in aqueous solution to degradation with a nuclease.

A. Cationic Lipids

Various suitable cationic lipids may be used in the SNALPs described herein, either alone or in combination with one or more other cationic lipid species or neutral lipid species.

Cationic lipids which are useful in the present invention can be any of a number of lipid species which carry a net positive charge at physiological pH, for example: DODAC, DOTMA, DDAB, DOTAP, DOSPA, DOGS, DC-Chol and DMRIE, or combinations thereof. A number of these lipids and related analogs, which are also useful in the present invention, have been described in U.S. Pat. Nos. 5,208,036, 5,264,618, 5,279,833, 5,283,185, 5,753,613 and 5,785,992, the disclosures of each of which are incorporated herein by reference.

The cationic lipid typically comprises from about 2% to about 60% of the total lipid present in said particle, preferably from about 5% to about 45% of the total lipid present in said particle. In certain preferred embodiments, the cationic lipid comprises from about 5% to about 15% of the total lipid present in said particle. In other preferred embodiments, the cationic lipid comprises from about 40% to about 50% of the total lipid present in said particle. Depending on the intended use of the nucleic acid-lipid particles, the proportions of the components are varied and the delivery efficiency of a particular formulation can be measured using an endosomal release parameter (ERP) assay. For example, for systemic delivery, the cationic lipid may comprise from about 5% to about 15% of the total lipid present in said particle and for local or regional delivery, the cationic lipid comprises from about 40% to about 50% of the total lipid present in said particle.

B. Noncationic Lipids

The noncationic lipid component of the SNALPs described herein can be any of a variety of neutral uncharged, zwitterionic or anionic lipids capable of producing a stable complex. They are preferably neutral, although they can alternatively be positively or negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), palmitoyloleyolphosphatidylglycerol (POPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in U.S. Pat. No. 5,820,873, incorporated herein by reference.

In preferred embodiments, the noncationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the noncationic lipid will include one or more of cholesterol, 1,2-sn-dioleoylphosphatidylethanolamine, or egg sphingomyelin (ESM).

The non-cationic lipid typically comprises from about 5% to about 90% of the total lipid present in said particle, preferably from about 20% to about 85% of the total lipid present in said particle. The PEG-DAG conjugate typically comprises from 1% to about 20% of the total lipid present in said particle, preferably from 4% to about 15% of the total lipid present in said particle. The nucleic acid-lipid particles of the present invention may further comprise cholesterol. If present, the cholesterol typically comprises from about 10% to about 60% of the total lipid present in said particle, preferably the cholesterol comprises from about 20% to about 45% of the total lipid present in said particle.

C. Bilayer Stabilizing Component

In one embodiment, the SNALP further comprises a bilayer stabilizing component (BSC). Suitable BSCs include, but are not limited to, polyamide oligomers, peptides, proteins, detergents, lipid-derivatives, PEG-lipids, such as PEG coupled to dialkyloxypropyls (PEG-DAA), PEG coupled to diacylglycerol (PEG-DAG), PEG coupled to phosphatidylethanolamine (PE) (PEG-PE), or PEG conjugated to ceramides, or a mixture thereof (see, U.S. Pat. No. 5,885,613, which is incorporated herein by reference). In one embodiment, the bilayer stabilizing component is a PEG-lipid, or an ATTA-lipid. In one preferred embodiment, the BSC is a conjugated lipid that inhibits aggregation of the SNALPs. Suitable conjugated lipids include, but are not limited to PEG-lipid conjugates, ATTA-lipid conjugates, cationic-polymer-lipid conjugates (CPLs) or mixtures thereof. In one preferred embodiment, the SNALPs comprise either a PEG-lipid conjugate or an ATTA-lipid conjugate together with a CPL.

Typically, the bilayer stabilizing component is present ranging from about 0.5% to about 50% of the total lipid present in the particle. In a preferred embodiment, the bilayer stabilizing component is present from about 0.5% to about 25% of the total lipid in the particle. In other preferred embodiments, the bilayer stabilizing component is present from about 1% to about 20%, or about 3% to about 15% or about 4% to about 10% of the total lipid in the particle. One of ordinary skill in the art will appreciate that the concentration of the bilayer stabilizing component can be varied depending on the bilayer stabilizing component employed and the rate at which the liposome is to become fusogenic.

By controlling the composition and concentration of the bilayer stabilizing component, one can control the rate at which the bilayer stabilizing component exchanges out of the liposome and, in turn, the rate at which the liposome becomes fusogenic. For instance, when a polyethyleneglycol-phosphatidylethanolamine conjugate or a polyethyleneglycol-ceramide conjugate is used as the bilayer stabilizing component, the rate at which the liposome becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the liposome becomes fusogenic. Other methods which can be used to control the rate at which the liposome becomes fusogenic will become apparent to those of skill in the art upon reading this disclosure.

1. Diacylglycerol-polyethyleneglycol Conjugates

In one embodiment, the bilayer stabilizing component comprises a diacylglycerol-polyethyleneglycol conjugate, i.e., a DAG-PEG conjugate or a PEG-DAG conjugate. In a preferred embodiment, the DAG-PEG conjugate is a dilaurylglycerol ($C_{12}$)-PEG conjugate, dimyristylglycerol ($C_{14}$)-PEG conjugate (DMG), a dipalmitoylglycerol ($C_{16}$)-PEG conjugate or a distearylglycerol ($C_{18}$)-PEG conjugate (DSG). Those of skill in the art will readily appreciate that other diacylglycerols can be used in the DAG-PEG conjugates of the present invention. Suitable DAG-PEG conjugates for use in the present invention, and methods of making and using them, are disclosed in U.S. application Ser. No. 10/136,707 published as U.S.P.A. 2003/0077829, and PCT Patent Application No. CA 02/00669, each of which is incorporated herein in its entirety by reference.

2. Dialkyloxypropyl Conjugates

In another embodiment, the bilayer stabilizing component comprises a dialkyloxypropyl conjugate, i.e., a PEG-DAA conjugate. In one preferred embodiment, the PEG-DAA conjugate has the following formula:

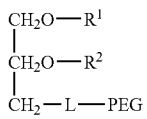
                      I

In Formula I, $R^1$ and $R^2$ are independently selected and are long-chain alkyl groups having from about 10 to about 22 carbon atoms. The long-chain alkyl groups can be saturated or unsaturated. Suitable alkyl groups include, but are not limited to, lauryl (C12), myristyl (C14), palmityl (C16), stearyl (C18) and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc. In Formula I, PEG is a polyethylene glycol having an average molecular weight of from about 550 to about 8,500 daltons. In a preferred embodiment, the PEG has an average molecular weight of from about 1000 to about 5000 daltons, more preferably, from about 1,000 to about 3,000 daltons and, even more preferably, of about 2,000 daltons. The PEG can be optionally, substituted by an alkyl, alkoxy, acyl or aryl group. In Formula I, L is a linker moiety. Any linker moiety suitable for coupling the PEG to the dialkyloxypropyl backbone can be used. Suitable linker moieties include, but are not limited to, amido (—C(O) NH—), amino (—NR—), carbonyl (—C(O)—), carbonate (O—C(O)O—), carbamate (—NHC(O)O—), urea (—NHC (O)NH—), succinyl (—(O)CCH$_2$CH$_2$C(O)—), ether, disulphide, and combinations thereof. Other suitable linkers are well known in the art.

Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidylethanolamine (DSPE).

As with the phosphatidylethanolamines, ceramides having a variety of acyl chain groups of varying chain lengths and degrees of saturation can be coupled to polyethyleneglycol to form the bilayer stabilizing component. It will be apparent to those of skill in the art that in contrast to the phosphatidylethanolamines, ceramides have only one acyl group which can be readily varied in terms of its chain length and degree of saturation. Ceramides suitable for use in accordance with the present invention are commercially available. In addition, ceramides can be isolated, for example, from egg or brain using well-known isolation techniques or, alternatively, they can be synthesized using the methods and techniques disclosed in U.S. Pat. No. 5,820,873, which is incorporated herein by reference. Using the synthetic routes set forth in the foregoing application, ceramides having saturated or unsaturated fatty acids with carbon chain lengths in the range of $C_2$ to $C_{31}$ can be prepared.

3. Cationic Polymer Lipids

Cationic polymer lipids (CPLs) can also be used in the SNALPS described herein. Suitable CPL typically have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group. Suitable SNALPs and SNALP-CPLs for use in the present invention, and methods of making and using SNALPs and SNALP-CPLs, are disclosed, e.g., in U.S. application Ser. Nos. 09/553,639 and 09/839,707 (published as U.S.P.A. 2002/ 0072121) and PCT Patent Application No. CA 00/00451 (published as WO 00/62813), each of which is incorporated herein in its entirety by reference.

Briefly, the present invention provides a compound of Formula II:

                      I wherein A, W and Y are as follows.

With reference to Formula II, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N—N-dialkylaminos, 1,2-diacyloxy-3-aminopropanes and 1,2-dialkyl-3-aminopropanes.

"W" is a polymer or an oligomer, such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers and combinations thereof. In a preferred embodiment, the polymer has a molecular weight of about 250 to about 7000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of liposome application which is desired.

The charges on the polycationic moieties can be either distributed around the entire liposome moiety, or alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A," and the nonimmunogenic polymer "W," can be attached by various methods and preferably, by covalent attachment. Methods known to those of skill in the art can be used for the covalent attachment of "A" and "W." Suitable linkages include, but are not limited to, amide, amine, carboxyl, carbonate, carbamate, ester and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. Pat. Nos. 6,320,017 and 6,586,559, both of which are incorporated herein by reference), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

D. siRNA

The nucleic acid component of the SNALPs typically comprise an interfering RNA (i.e., siRNA), which can be provided in several forms including, e.g. as one or more isolated small-interfering RNA (siRNA) duplexes, longer double-stranded RNA (dsRNA) or as siRNA or dsRNA transcribed from a transcriptional cassette in a DNA plasmid.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtrated, selected etc.), or can represent a single target sequence. RNA can be naturally occurring, e.g., isolated from tissue or cell samples, synthesized in vitro, e.g., using T7 or SP6 polymerase and PCR products or a cloned cDNA; or chemically synthesized.

To form a long dsRNA, for synthetic RNAs, the complement is also transcribed in vitro and hybridized to form a ds RNA. If a naturally occuring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directlu emcapsulated in the SNALPs or can be digested in vitro prior to encapsulation.

Alternatively, one or more DNA plasmids encoding one or more siRNA templates are encapsulated in a nucleic acid-lipid particle. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., *Science* 296: 550 (2002); Donzé, et al., *Nucleic Acids Res.* 30:e46 (2002); Paddison, et al., *Genes Dev.* 16:948 (2002); Yu, et al., *Proc. Natl. Acad. Sci.* 99:6047 (2002); Lee, et al., *Nat. Biotech.* 20:500 (2002); Miyagishi, et al., *Nat. Biotech.* 20:497 (2002); Paul, et al., *Nat. Biotech.* 20:505 (2002); and Sui, et al., *Proc. Natl. Acad. Sci.* 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp, *Science*, supra). The selected promoter can provide for constitutive or inducible transcription. Compositions and methods for DNA-directed transcription of RNA interference molecules is described in detail in U.S. Pat. No. 6,573,099, incorporated herein by reference. Preferably, the synthesized or transcribed siRNA have 3' overhangs of about 1-4 nucleotides, preferably of about 2-3 nucleotides and 5' phosphate termini (Elbashir, et al., *Genes Dev.* 15:188 (2001); Nykänen, et al., *Cell* 107:309 (2001)). The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488, both of which are incorporated herein by reference. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler & Hoffman, *Gene* 25:263-269 (1983); Sambrook et al., supra; Ausubel et al., supra), as are PCR methods (see U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

1. Target Genes

Generally, it is desired to deliver the SNALPS to down-regulate or silence the translation (i.e., expression) of a gene product of interest. Suitable classes of gene products include, but are not limited to, genes associated with viral infection and survival, genes associated with metabolic dieases and disorders (e.g., diseases and disorders in which the liver is the target, and liver diseases and disorders) and disorders, genes associated with tumorigenesis and cell transformation, angiogenic genes, immunomodulator genes, such as those associated with inflammatory and autoimmune responses, ligand receptor genes, and genes associated with neurodegenerative disorders.

Genes associated with viral infection and survival include those expressed by a virus in order to bind, enter and replicate in a cell. Of particular interest are viral sequences associated with chronic viral diseases. Viral sequences of particular interest include sequences of Hepatitis viruses (Hamasaki, et al., *FEBS Lett.* 543:51 (2003); Yokota, et al., *EMBO Rep.* 4:602 (2003); Schlomai, et al., *Hepatology* 37:764 (2003); Wilson, et al., *Proc. Natl. Acad. Sci.* 100:2783 (2003); Kapadia, et al., *Proc. Natl. Acad. Sci.* 100:2014 (2003); and FIELDS VIROLOGY (Knipe et al. eds. 2001)), Human Immunodeficiency Virus (HIV) (Banerjea, et al., *Mol. Ther.* 8:62 (2003); Song, et al., *J. Virol.* 77:7174 (2003); Stephenson *JAMA* 289: 1494 (2003); Qin, et al., *Proc. Natl. Acad. Sci.* 100:183 (2003)), Herpes viruses (Jia, et al., *J. Virol.* 77:3301 (2003)), and Human Papilloma Viruses (HPV) (Hall, et al., *J. Virol.* 77:6066 (2003); Jiang, et al., *Oncogene* 21:6041 (2002)). Examplary hepatitis viral nucleic acid sequences that can be silenced include but are not limited to: nucleic acid sequences involved in transcription and translation (e.g., En1, En2, X, P), nucleic acid sequences encoding structural proteins (e.g., core proteins including C and C-related proteins; capsid and envelope proteins including S, M, and/or L proteins, or fragments thereof) (see, e.g., FIELDS VIROLOGY, 2001, supra). Exemplary Hepatits C nucleic acid sequences that can be silenced include but are not limited to: serine proteases (e.g., NS3/NS4), helicases (e.g. NS3), polymerases (e.g., NS5B), and envelope proteins (e.g., E1, E2, and p7). Hepatitis A nucleic acid sequences are set forth in e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in e.g., Genbank Accession No. NC_001434; and Hepatitis G nucleic acid sequences are set forth in e.g., Genbank Accession No. NC_001710. Silencing of sequences that encode genes associated with viral infection and survival can conveniently be used in combination with the administration of conventional agents used to treat the viral condition.

Genes associated with metabolic diseases and disorders (e.g., disorders in which the liver is the target and liver diseases and disorders) include, for example genes expressed in, for example, dyslipidemia (e.g., liver X receptors (e.g., LXRα and LXRβ Genback Accession No. NM_007121), farnesoid X receptors (FXR) (Genbank Accession No. NM_005123), sterol-regulatory element binding protein (SREBP), Site-1 protease (S1P), 3-hydroxy-3-methylglutaryl coenzyme-A reductase (HMG coenzyme-A reductase), Apolipoprotein (ApoB), and Apolipoprotein (ApoE)) and diabetes (e.g., Glucose 6-phosphatase) (see, e.g., Forman et al., *Cell* 81:687 (1995); Seol et al., *Mol. Endocrinol.* 9:72 (1995), Zavacki et al., *PNAS USA* 94:7909 (1997); Sakai, et al., *Cell* 85:1037-1046 (1996); Duncan, et al., *J. Biol. Chem.* 272:12778-12785 (1997); , Willy, et al., *Genes Dev.* 9(9): 1033-45 (1995); Lehmann, et al., *J. Biol. Chem.* 272(6):3137-3140 (1997); Janowski, et al., *Nature* 383:728-731 (1996); Peet, et al., *Cell* 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder.

Examples of gene sequences associated with tumorigenesis and cell transformation include translocation sequences such as MLL fusion genes, BCR-ABL (Wilda, et al., *Oncogene*, 21:5716 (2002); Scherr, et al., *Blood* 101: 1566), TEL-AML1, EWS-FLI1, TLS-FUS, PAX3-FKHR, BCL-2, AML1-ETO and AML1-MTG8 (Heidenreich, et al., *Blood* 101:3157 (2003)); overexpressed sequences such as multidrug resistance genes (Nieth, et al., *FEBS Lett.* 545:144 (2003); Wu, et al, *Cancer Res.* 63:1515 (2003)), cyclins (Li, et al., *Cancer Res.* 63:3593 (2003); Zou, et al., *Genes Dev.* 16:2923 (2002)), beta-Catenin (Verma, et al., *Clin Cancer Res.* 9:1291 (2003)), telomerase genes (Kosciolek, et al., *Mol Cancer Ther.* 2:209 (2003)), c-MYC, N-MYC, BCL-2, ERBB1 and ERBB2 (Nagy, et al. *Exp. Cell Res.* 285:39 (2003)); and mutated sequences such as RAS (reviewed in Tuschl and Borkhardt, *Mol. Interventions,* 2:158 (2002)). Silencing of sequences that encode DNA repair enzymes find use in combination with the administration of chemotherapeutic agents (Collis, et al., *Cancer Res.* 63:1550 (2003)). Genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a template sequence Angiogenic genes are able to promote the formation of new vessels. Of particular interest is Vascular Endothelial Growth Factor (VEGF) (Reich, et al., *Mol. Vis.* 9:210 (2003)).

Immunomodulator genes are genes that modulate one or more immune responses. Examples of immunomodulator genes include cytokines such as growth factors (e.g., TGF-α., TGF-β, EGF, FGF, IGF, NGF, PDGF, CGF, GM-CSF, SCF, etc.), interleukins (e.g., IL-2, IL-4, IL-12 (Hill, et al., *J. Immunol.* 171:691 (2003)), IL-15, IL-18, IL-20, etc.), interferons (e.g., IFN-α, IFN-β, IFN-γ, etc.) and TNF. Fas and Fas Ligand genes are also immunomodulator target sequences of interest (Song, et al., *Nat. Med.* 9:347 (2003)). Genes encoding secondary signaling molecules in hematopoietic and lymphoid cells are also included in the present invention, for example, Tec family kinases, such as Bruton's tyrosine kinase (Btk) (Heinonen, et al., *FEBS Lett.* 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). Templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease (Caplen, et al., *Hum. Mol. Genet.* 11:175 (2002)).

IV. Preparation of SNALPs

The present invention provides methods for preparing serum-stable nucleic acid-lipid particles such that the nucleic acid (e.g., siRNA or plasmid encoding siRNA) is encapsulated in a lipid bilayer and is protected from degradation. The SNALPs made by the methods of this invention are typically about 50 to about 150 nm in diameter. They generally have a median diameter of less than about 150 nm, more typically a diameter of less than about 100 nm, with a majority of the particles having a median diameter of about 65 to 85 rm. The particles can be formed by using any method known in the art including, e.g., a detergent dialysis method or by modification of a reverse-phase method which utilizes organic solvents to provide a single phase during mixing of the components. Without intending to be bound by any particular mechanism of formation, a plasmid or other nucleic acid (i.e., siRNA) is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, noncationic lipids) to form particles in which the plasmid or other nucleic acid is encapsulated in a lipid bilayer. The methods described below for the formation of nucleic acid-lipid particles using organic solvents follow a similar scheme. Exemplary methods of making SNALPS are disclosed in U.S. Pat. Nos. 5,705,385; 5,981,501; 5,976,567; 6,586,410; 6,534,484; U.S. application Ser. No. 09/553,639; U.S.P.A. Publication Nos. 2002/0072121 and 2003/0077829) WO 96/40964; and WO 00/62813.

In one embodiment, the present invention provides nucleic acid-lipid particles produced via a process that includes providing an aqueous solution in a first reservoir, and providing an organic lipid solution in a second reservoir, and mixing the aqueous solution with the organic lipid solution such that the organic lipid solution mixes with the aqueous solution so as to substantially instantaneously produce a liposome encapsulating the nucleic acid. This process and the apparatus for carrying this process is described in detail in U.S. patent application Ser. No. 10/611,274 filed Jun. 30, 2003, which is incorporated herein by reference.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in an hydration process with sufficient force to effectuate vesicle generation. By mixing the aqueous solution with the organic lipid solution, the organic lipid solution undergoes a continuous stepwise dilution in the presence of the buffer (aqueous) solution to produce a liposome.

In some embodiments, the particles are formed using detergent dialysis. Thus, the present invention provides a method for the preparation of serum-stable nucleic acid-lipid particles, comprising:

(a) combining a nucleic acid with cationic lipids in a detergent solution to form a coated nucleic acid-lipid complex;

(b) contacting noncationic lipids with the coated nucleic acid-lipid complex to form a detergent solution comprising a nucleic acid-lipid complex and noncationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol)ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of nucleic acid in solution will typically be from about 25 µg/mL to about 1 mg/mL, preferably from about 25 µg/mL to about 200 µg/mL, and more preferably from about 50 µg/mL to about 100 µg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C. For nucleic acids which are particularly sensitive to temperature, the coated complexes can be formed at lower temperatures, typically down to about 4° C.

In a preferred embodiment, the nucleic acid to lipid ratios (mass/mass ratios) in a formed SNALP will range from about 0.01 to about 0.08. The ratio of the starting materials also falls within this range because the purification step typically removes the unencapsulated nucleic acid as well as the empty liposomes. In another preferred embodiment, the SNALP preparation uses about 400 µg nucleic acid per 10 mg total lipid or a nucleic acid to lipid ratio of about 0.01 to about 0.08 and, more preferably, about 0.04, which corresponds to 1.25 mg of total lipid per 50 µg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. In addition, the nucleic acid-lipid particles of the present invention may further comprise cholesterol. In other preferred embodiments, the noncationic lipids will further comprise polyethylene glycol-based polymers such as PEG 2000, PEG 5000 and polyethylene glycol conjugated to a diacylglycerol, a ceramide or a phospholipid, as described in U.S. Pat. No. 5,820,873 and in co-pending patent application Ser. No. 10/136,707 (published as U.S.P.A. Publication No. 2003/0077829), both of which are incorporated herein by reference. In further preferred embodiments, the noncationic lipids will further comprise polyethylene glycol-based polymers such as PEG 2000, PEG 5000 and polyethylene glycol conjugated to a dialkyloxypropyl.

The amount of noncationic lipid which is used in the present methods is typically about 2 to about 20 mg of total lipids to 50 μg of nucleic acid. Preferably the amount of total lipid is from about 5 to about 10 mg per 50 μg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323, incorporated herein by reference. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable nucleic acid-lipid particles, comprising:
(a) preparing a mixture comprising cationic lipids and non-cationic lipids in an organic solvent;
(b) contacting an aqueous solution of nucleic acid with said mixture in step (a) to provide a clear single phase; and
(c) removing said organic solvent to provide a suspension of nucleic acid-lipid particles, wherein said nucleic acid is encapsulated in a lipid bilayer, and said particles are stable in serum and have a size of from about 50 to about 150 nm.

The nucleic acids (or plasmids), cationic lipids and nonationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, iso-propanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to 150 nm. To achieve further size reduction or homogeneity of size in the particles, sizing can be conducted as described above.

In other embodiments, the methods will further comprise adding nonlipid polycations which are useful to effect the delivery to cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the present invention provides a method for the preparation of nucleic acid-lipid particles, comprising:
(a) contacting nucleic acids with a solution comprising noncationic lipids and a detergent to form a nucleic acid-lipid mixture;
(b) contacting cationic lipids with the nucleic acid-lipid mixture to neutralize a portion of the negative charge of the nucleic acids and form a charge-neutralized mixture of nucleic acids and lipids; and
(c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

In some embodiments, the nucleic acids are precondensed as described in, e.g., U.S. patent application Ser. No. 09/744, 103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DODAC, DOTMA, DDAB, DOTAP, DC-Chol and DMRIE. These lipids and related analogs have been described in U.S. Pat. Nos. 5,208,036, 5,264,618, 5,279,833, 5,283,185, 5,753,613 and 5,785,992, the disclosures of each of which are incorporated herein by reference.

Contacting the cationic lipids with the nucleic acid-lipid mixture can be accomplished by any of a number of techniques, preferably by mixing together a solution of the cationic lipid and a solution containing the nucleic acid lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 100 nm to several microns. To achieve further size reduction or homogeneity of size in the particles, the nucleic acid-lipid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of nucleic acid-lipid particles, comprising:
 (a) contacting an amount of cationic lipids with nucleic acids in a solution; the solution comprising from about 15-35% water and about 65-85% organic solvent and the amount of cationic lipids being sufficient to produce a +/− charge ratio of from about 0.85 to about 2.0, to provide a hydrophobic nucleic acid-lipid complex;
 (b) contacting the hydrophobic, nucleic acid-lipid complex in solution with non-cationic lipids, to provide a nucleic acid-lipid mixture; and
 (c) removing the organic solvents from the nucleic acid-lipid mixture to provide nucleic acid-lipid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the cationic lipids are DODAC, DDAB, DOTMA, DOSPA, DMRIE, DOGS or combinations thereof. In other preferred embodiments, the noncationic lipids are ESM, DOPE, DOPC, DSPC, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether or combinations thereof.

In one embodiment, the nucleic acid is a plasmid from which an interfering RNA is transcribed; the cationic lipid is DODAC, DDAB, DOTMA, DOSPA, DMRIE, DOGS or combinations thereof; the noncationic lipid is ESM, DOPE, DAG-PEGs, distearoylphosphatidylcholine (DSPC), cholesterol, or combinations thereof (e.g. DSPC and DAG-PEGs); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In yet another aspect, the present invention provides nucleic acid-lipid particles which are prepared by the methods described above. In these embodiments, the nucleic acid-lipid particles are either net charge neutral or carry an overall charge which provides the particles with greater gene lipofection activity. Preferably, the nucleic acid component of the particles is a nucleic acid which interferes with the production of an undesired protein. In a preferred embodiment, the nucleic acid comprises an interfering RNA, the noncationic lipid is egg sphingomyelin and the cationic lipid is DODAC. In a preferred embodiment, the nucleic acid comprises an interfering RNA, the noncationic lipid is a mixture of DSPC and cholesterol, and the cationic lipid is DOTMA. In other preferred embodiments, the noncationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results, in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAGs). Methods of making SNALP-CPL are taught, for example, in U.S. Pat. Nos. 5,705,385, 6,586,410, 5,981,501 and 6,534,484; in U.S. application Ser. Nos. 09/553,639 and 09/839,707 (published as U.S.P.A. Publication No. 2002/0072121), as well as in PCT International Application PCT/CA00/00451 (published as WO 00/62813), each of which is incorporated herein by reference.

The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2.5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis associated congestive heart failure or severe hypertension. Alternatively, particles composed of irritating lipids may be diluted to low concentrations to lessen inflammation at the site of administration.

As described above, in some embodiments of the present invention the nucleic acid-lipid particles comprise DAG-PEG conjugates. In other embodiments, of the invention, the nucleic acid-lipid particles comprise PEG-dialkyloxypropyl conjugates. It is often desirable to include other components that act in a manner similar to the DAG-PEG conjugates or PEG-dialkyloxypropyl conjugates and that serve to prevent particle aggregation and to provide a means for increasing circulation lifetime and increasing the delivery of the nucleic acid-lipid particles to the target tissues. Such components include, but are not limited to, PEG-lipid conjugates, such as PEG-ceramides or PEG-phospholipids (such as PEG-PE), ganglioside GM1-modified lipids or ATTA-lipids to the particles. Typically, the concentration of the component in the particle will be about 1-20% and, more preferably from about 3-10%.

The pharmaceutical compositions of the present invention may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

V. Administration of SNALPs

The SNALPs of the present invention can conveniently be used to introduce nucleic acids into cells (e.g., to treat or prevent a disease or disorder associated with expression of a target gene). Accordingly, the present invention also provides methods for introducing a nucleic acid (e.g., an interfering RNA) into a cell. The methods are carried out in vitro or in vivo by first forming the particles as described above, then contacting the particles with the cells for a period of time sufficient for delivery of siRNA to occur.

The SNALPs of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

Among the cell types most often targeted for intracellular delivery of a siRNA are neoplastic cells (e.g. tumor cells) and hepatocytes. Other cells that can be targeted, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like. In a preferred embodiment, hepatocytes are targeted.

To the extent that tissue culture of cells may be required, it is well known in the art. Freshney (1994) (Culture of Animal Cells, a Manual of Basic Technique, third edition Wiley-Liss, New York), Kuchler et al. (1977) Biochemical Methods in Cell Culture and Virology, Kuchler, R. J., Dowden, Hutchinson and Ross, Inc., and the references cited therein provides a general guide to the culture of cells. Cultured cell systems often will be in the form of monolayers of cells, although cell suspensions are also used.

A. In Vitro Gene Transfer

For in vitro applications, the delivery of siRNA can be to any cell grown in culture, whether of plant or animal origin, vertebrate or invertebrate, and of any tissue or type. In preferred embodiments, the cells will be animal cells, more preferably mammalian cells, and most preferably human cells.

Contact between the cells and the lipid nucleic acid particles, when carried out in vitro, takes place in a biologically compatible medium. The concentration of particles varies widely depending on the particular application, but is generally between about 1 mmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a lipid nucleic acid particle suspension is added to 60-80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 μg/mL, more preferably about 0.1 μg/mL.

Using an Endosomal Release Parameter (ERP) assay, the delivery efficiency of the SNALP or other lipid-based carrier system can be optimized. An ERP assay is described in detail in U.S. patent application Ser. No. 10/136,707 (published as U.S.P.A. Publication No. 2003/0077829), incorporated herein by reference. More particularly, the purpose of an ERP assay is to distinguish the effect of various cationic lipids and helper lipid components of SNALPs based on their relative effect on binding/uptake or fusion with/destabilization of the endosomal membrane. This assay allows one to determine quantitatively how each component of the SNALP or other lipid-based carrier system effects delivery efficiency, thereby optimizing the SNALPs or other lipid-based carrier systems. Usually, an ERP assay measures expression of a reporter protein (e.g., luciferase, β-galactosidase, green fluorescent protein, etc.), and in some instances, a SNALP formulation optimized for an expression plasmid will also be appropriate for encapsulating an interfering RNA. In other instances, an ERP assay can be adapted to measure downregulation of translation of a target sequence in the presence or absence of an interfering RNA. By comparing the ERPs for each of the various SNALPs or other lipid-based formulations, one can readily determine the optimized system, e.g., the SNALP or other lipid-based formulation that has the greatest uptake in the cell.

Suitable labels for carrying out the ERP assay of the present invention include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3H$, $^{125}I$, $^{35}S$, $^{14}C$, $^{32}P$, $^{33}P$, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the SNALP or other lipid-based carrier system using methods well known in the art. As indicated above, a wide variety of labels can be used, with the choice of label depending on sensitivity required, ease of conjugation with the SNALP component, stability requirements, and available instrumentation and disposal provisions.

B. In Vivo Gene Transfer

In some embodiments, the SNALPs can be used for in vivo delivery of siRNA to a wide variety of vertebrates, including mammals such as canines, felines, equines, bovines, ovines, caprines, rodents, lagomorphs, swines, primates, including, e.g., humans. In vivo delivery of the SNALPs may be local (i.e., directly to the site of interest) or systemic (i.e., distal from the site of interest).

Systemic delivery for in vivo gene therapy, i.e., delivery of a therapeutic nucleic acid to a distal target cell via body systems such as the circulation, has been achieved using nucleic acid-lipid particles such as those disclosed in published PCT Patent Application WO 96/40964, U.S. Pat. Nos. 5,705,385, 5,976,567, 5,981,501, and 6,410,328, each of which are incorporated herein by reference. This latter format provides a fully encapsulated nucleic acid-lipid particle that protects the nucleic acid from nuclease degradation in serum, is nonimmunogenic, is small in size and is suitable for repeat dosing.

The SNALPs of the present invention can be administered via any route known in the art including, e.g., intravenously, intramuscularly, subcutaneously, intradermally, intraperitoneally, orally, intranasally, or topically. For example, Zhu, et al., Science 261:209 (1993) describes the intravenous delivery of plasmid-cationic lipid complexes; Hyde, et al., Nature 362:250 (1993) describes intranasal delivery of plasmid-liposome complexes (i.e., lipoplexes); and Brigham, et al., Am. J. Med. Sci. 298:278 (1989), describes intravenous and intratracheal delivery of plasmid-cationic lipid complexes. The SNALPs may be administered alone or in mixture with a physiologically-acceptable carrier (such as physiological saline or phosphate buffer) selected in accordance with the route of administration and standard pharmaceutical practice.

When preparing pharmaceutical preparations of the nucleic acid-lipid particles of the invention, it is preferable to use quantities of the nucleic acid-lipid particles which have been purified to reduce or eliminate empty lipid particles or particles with nucleic acid portion associated with the external surface. The pharmaceutical carrier is generally added following particle formation. Thus, after the particle is formed, the particle can be diluted into pharmaceutically acceptable carriers.

The concentration of particles in the pharmaceutical formulations can vary widely, i.e., from less than about 0.05%, usually at or at least about 2.5% to as much as 10 to 30% by weight and will be selected primarily by fluid volumes, viscosities, etc., in accordance with the particular mode of administration selected.

The amount of particles administered will depend upon the ratio of nucleic acid to lipid; the particular nucleic acid used, the disease state being diagnosed; the age, weight, and condition of the patient and the judgment of the clinician; but will generally be between about 0.01 and about 50 mg per kilogram of body weight; preferably between about 0.1 and about 5 mg/kg of body weight or about $10^8$-$10^{10}$ particles per injection.

1. Injectable Delivery

In certain circumstances it will be desirable to deliver the SNALPs disclosed herein parenterally, intravenously, intramuscularly, subcutaneously, intradermally, or intraperitoneally as described in U.S. Pat. Nos. 5,543,158; 5,641,515 and 5,399,363. The SNALPs may be locally injected to the site of interest (e.g., a site of disease such as inflammation or neoplasia or to a target organ or tissue) or systemically injected for broad distribution throughout the organism. Solutions of the SNALPs may be prepared in water suitably mixed with a surfactant. Dispersions may also be prepared in glycerol, liquid polyethylene glycols, and mixtures thereof and in oils. Typically, these preparations contain a preservative to prevent the growth of microorganisms. Generally, when administered intravenously, the nucleic acid-lipid particles formulations are formulated with a suitable pharmaceutical carrier. Generally, normal buffered saline (135-150 mM NaCl) will be employed as the pharmaceutically acceptable carrier, but other suitable carriers will suffice. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

2. Oral Delivery

In certain applications, the SNALPs disclosed herein may be delivered via oral administration to the individual. The active compounds may even be incorporated with excipients and used in the form of ingestible tablets, buccal tablets, troches, capsules, elixirs, mouthwash, suspensions, oral sprays, syrups, wafers, and the like (Mathiowitz et al., 1997; Hwang et al., 1998; U.S. Pat. Nos. 5,641,515; 5,580,579 and 5,792,451). The tablets, troches, pills, capsules and the like may also contain the following: binders, gelatin; excipients, lubricants, or flavoring agents. When the dosage unit form is a capsule, it may contain, in addition to materials of the above type, a liquid carrier. Various other materials may be present as coatings or to otherwise modify the physical form of the dosage unit. Of course, any material used in preparing any dosage unit form should be pharmaceutically pure and substantially non-toxic in the amounts employed.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

3. Nasal Delivery

In certain embodiments, the pharmaceutical compositions may be delivered by intranasal sprays, inhalation, and/or other aerosol delivery vehicles. Methods for delivering nucleic acid compositions directly to the lungs via nasal aerosol sprays has been described e.g., in U.S. Pat. Nos. 5,756,353 and 5,804,212. Likewise, the delivery of drugs using intranasal microparticle resins (Takenaga et al., 1998) and lysophosphatidyl-glycerol compounds (U.S. Pat. No. 5,725,871) are also well-known in the pharmaceutical arts. Likewise, transmucosal drug delivery in the form of a polytetrafluoroethey-lene support matrix is described in U.S. Pat. No. 5,780,045.

4. Topical Delivery

In another example of their use, nucleic acid-lipid particles can be incorporated into a broad range of topical dosage forms including, but not limited to, gels, oils, emulsions and the like. For instance, the suspension containing the nucleic acid-lipid particles can be formulated and administered as topical creams, pastes, ointments, gels, lotions and the like.

C. Prophylactic and Therapeutic Treatment

In some embodiments, the SNALPs can be used for prophylactic or therapeutic treatment of subjects (e.g., mammalian subjects) with a disease or disorder associated with expression or overexpression of a target sequence. The SNALPs are administered to the subject in an amount sufficient to elicit a therapeutic response in the patient. An amount adequate to accomplish this is defined as "therapeutically effective dose or amount" or "effective dose or amount." In determining the effective amount of the SNALP to be administered in the treatment or prophylaxis of conditions owing to expression or overexpression of the target gene, the physician evaluates circulating plasma levels of the SNALPs, SNALP toxicities, and progression of the disease associated with expression or overexpression of the target gene. Administration can be accomplished via single or divided doses.

For example, the SNALP can be administered to a subject infected with, or at risk of being infected with a pathogenic microorganism. The siRNA should preferably correspond to a sequence that plays an essential role in the lifecycle of the microorganism, and should also be unique to the microorganism (or at least absent from the genome of the natural genome of a patient undergoing therapy). The nucleic acid-lipid complex is introduced into target cells, tissue, or organs, either ex vivo or by intravenous injection in a therapeutically effective dose. Silencing of sequences that encode genes associated with pathogenic infection can conveniently be used in combination with the administration of conventional agents used to treat the pathogenic condition. The treatment can be administered prophylactically to persons at risk of being infected with the pathogenic microorganism or to persons already infected with the pathogenic microorganism.

In a preferred embodiment, the compositions and methods of the invention can conveniently be used to treat liver disorders such as, for example, hepatitis. For example, suitable sites for inhibition on the Hepatitis B virus include nucleic acids sequences encoding S, C, P, and X proteins, PRE, EnI, and EnII (see, e.g., FIELDS VIROLOGY, 2001, supra).) One of skill in the art will appreciate that silencing of genes associated with hepatitis infection can be combined with conventional treatments for hepatitis such as, for example, immune globulin, interferon (e.g., pegylated and unpegylated interferon $\alpha$) (see, e.g., Medina et al., *Antiviral Res.* 60(2):135-143 (2003); ribavirin (see, e.g., Hugle and Cerny, *Rev. Med. Virol.* 13(6): 361-71(2003); adefovir and lamivudine (see, e.g., Kock et al., *Hepatology* 38(6):1410-8 (2003); prenylation inhibitors (see, e.g., Bordier et al., *J. Clin. Invest.* 112(3): 407-414 (2003)); famciclovir (see, e.g., Yurdaydin et al., *J Hepatol.* 37(2):266-71 (2002); and saikosaponins c and d (see, e.g., Chiang et al., *Planta Med.* 69(8):705-9 (2003).

In another exemplary embodiment, the pathogenic microorganism is HIV. For example, suitable sites for inhibition on the HIV virus include TAR, REV or nef (Chatterjee et al., *Science* 258:1485-1488 (1992)). Rev is a regulatory RNA binding protein that facilitates the export of unspliced HIV pre-mRNA from the nucleus. Malim et al., *Nature* 338:254 (1989). Tat is thought to be a transcriptional activator that functions by binding a recognition sequence in 5' flanking mRNA. Karn & Graeble, *Trends Genet.* 8:365 (1992). The nucleic acid-lipid complex is introduced into leukocytes or hemopoietic stem cells, either ex vivo or by intravenous injection in a therapeutically effective dose. The treatment can be administered prophylactically to persons at risk of being infected with HIV, or to persons already infected with HIV. Analogous methods are used for suppressing expression of endogenous recipient cell genes encoding adhesion proteins.

In another embodiment, the compositions and methods of the invention can conveniently be used to treat diseases and disorders characterized by expression or overexpression of a gene or group of genes. In some aspects, the compositions and methods of the invention can be used to treat metabolic diseases and disorders (e.g., diseases and disorders in which the liver is a target and liver diseases and disorders) such as, for example, dyslipidemia and diabetes. One of skill in the art will appreciate that silencing of genes associated with metabolic diseases and disorders can be combined with conventional treatments for these disorders. For example, silencing of genes involved in dyslipidemia can be combined treatment with, for example, statins, bile acid sequestrants/resins and cholesterol absorption inhibitors such as ezetimibe, plant stanols/sterols, polyphenols, as well as nutraceuticals such as oat bran, psyllium and soy proteins, phytostanol analogues, squalene synthase inhibitors, bile acid transport inhibitors SREBP cleavage-activating protein (SCAP) activating ligands, nicotinic acid (niacin), acipimox, high-dose fish oils, antioxidants and policosanol, microsomal triglyceride transfer protein (MTP) inhibitors, acylcoenzyme A: cholesterol acyltransferase (ACAT) inhibitors, gemcabene, lifibrol, pantothenic acid analogues, nicotinic acid-receptor agonists, anti-inflammatory agents (such as Lp-PLA(2) antagonists and AGI1067) functional oils, PPAR-$\alpha$, -$\gamma$, -$\delta$ agonists, as well as dual PPAR-$\alpha$,/$\gamma$ and 'pan' PPAR-$\alpha$/$\gamma$/$\delta$ agonists, cholesteryl ester transfer protein (CETP) inhibitors (such as torcetrapib), CETP vaccines, upregulators of ATP-binding cassette transporter (ABC) A1, lecithin cholesterol acyltransferase (LCAT) and scavenger receptor class B Type 1 (SRB1), as well as synthetic apolipoprotein (Apo)E-related peptides, extended-release niacin/lovastatin, atorvastatin/amlodipine, ezetimibe/simvastatin, atorvastatin/CETP inhibitor, statin/PPAR agonist, extended-release niacin/simvastatin and pravastatin/aspirin are under development, and anti-obesity agents. (see, e.g., Bays and Stein, *Expert Opin. Pharmacother.* 4(11):1901-38 (2003)). Likewise, silencing of genes involved in diabetes can be combined with treatment with insulin as well as diet modification and exercise.

Analogous methods are used for suppressing expression of endogenous recipient cell genes associated with tumorigenesis and cell transformation, tumor growth, and tumor migration; angiogenic genes; immunomodulator genes, such as those associated with inflammatory and autoimmune responses; ligand receptor genes; genes associated with neurodegenerative disorders; and additional genes associated with viral infection and survival. Target gene sequences of particular interest are described supra.

D. Detection of SNALPs

In some embodiments, the nucleic acid-lipid particles are detectable in the plasma and/or cells of the subject 8, 12, 24, 36, 48, 60, 72, 84, or 96 hours after administration of the particles. The presence of the particles can be detected by any means known in the art including, for example, direct detection of the particles, detection of the interfering RNA sequence, detection of the target sequence of interest (i.e., by detecting expression or reduced expression of the sequence of interest), or a combination thereof.

1. Detection of Particles

Nucleic acid-lipid particles are detected herein using any methods known in the art. For example, a label can be coupled directly or indirectly to a component of the SNALP or other lipid-based carrier system using methods well known in the art. A wide variety of labels can be used, with the choice of label depending on sensitivity required, ease of conjugation with the SNALP component, stability requirements, and available instrumentation and disposal provisions. Suitable labels include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be detected using any means, known in the art.

2. Detection of Nucleic Acids

Nucleic acids are detected and quantified herein by any of a number of means well known to those of skill in the art. The detection of nucleic acids proceeds by well known methods such as Southern analysis, northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), hyperdiffusion chromatography, may also be employed The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Q$\beta$-replicase amplification and other RNA polymerase mediated techniques (e.g., NASBA™) are found in Sambrook, et al., In *Molecular Cloning: A Laboratory Manual*, Cold Spring Harbor Laboratory Press, 2000, and Ausubel et al., SHORT PROTOCOLS IN MOLECULAR BIOLOGY, eds., Current Protocols, a joint venture between Greene Publishing Associates, Inc. and John Wiley & Sons, Inc., (2002), as well as Mullis et al. (1987), U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990), *C&EN* 36; The *Journal Of NIH Research*, 3:81 (1991); (Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990), and Sooknanan and Malek, *Biotechnology*, 13:563 (1995). Improved methods of cloning in vitro amplified nucleic acids are described in Wallace et al., U.S. Pat. No. 5,426,039. Other methods described in the art are the nucleic acid sequence based amplification (NASBA™, Cangene, Mississauga, Ontario) and Q Beta Replicase systems.

Oligonucleotides for use as probes, e.g., in in vitro amplification methods, for use as gene probes, or as inhibitor components are typically synthesized chemically according to the solid phase phosphoramidite triester method described by Beaucage and Caruthers, *Tetrahedron Letts.*, 22(20):1859 1862 (1981), e.g., using an automated synthesizer, as described in Needham VanDevanter et al., *Nucleic Acids Res.*, 12:6159 (1984). Purification of oligonucleotides, where necessary, is typically performed by either native acrylamide gel electrophoresis or by anion exchange HPLC as described in Pearson and Regnier, *J. Chrom.*, 255:137 149 (1983). The sequence of the synthetic oligonucleotides can be verified using the chemical degradation method of Maxam and Gilbert (1980) in Grossman and Moldave (eds.) Academic Press, New York, *Methods in Enzymology*, 65:499.

An alternative means for determining the level of translation is in situ hybridization. In situ hybridization assays are well known and are generally described in Angerer et al., *Methods Enzymol.*, 152:649 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

VI. Kits

The present invention also provides nucleic acid-lipid particles in kit form. The kit will typically be comprised of a container which is compartmentalized for holding the various elements of the nucleic acid-lipid particles and the endosomal membrane destabilizer (e.g., calcium ions). The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

EXAMPLES

The following examples are offered to illustrate, but not to limit the claimed invention. Those of skill in the art will readily recognize a variety of noncritical parameters which can be changed or modified to yield essentially the same results.

Example 1

SNALP Formulations Encapsulating siRNA

This example demonstrates encapsulating siRNA in SNALP formulated with either short- or long-chain PEG-DAG and produced by continuously mixing organic lipid and aqueous buffer solutions. PEG-DAG lipids employed were PEG-dimyristylglycerol ($C_{14}$) (PEG-DMG) and PEG-distearylglycerol ($C_{18}$) (PEG-DSG). Anti-β-galactosidase (β-gal) siRNA encapsulated in DSPC:Cholesterol:DODMA: PEG-DMG/PEG-DSG SNALP by this method resulted in ≧90% encapsulation (Ribogreen Assay) and ~120 nm particle size (Malvern sizer). The preparations had the following characteristics:

4 ml prep: anti-B-gal siRNA in DSPC:Chol:DODMA:PEG-DMG liposomes
 Initial mix=94% encapsulation
 Post dilution mix=98% encapsulation
 Post incubation mix=97% encapsulation
 Post overnight dialysis=96% encapsulation
 Particle size=109.7 nm
 Polydispersity=0.14

8 ml prep: anti-B-gal siRNA in DSPC:Chol:DODMA:PEG-DMG liposomes
 Post dilution & incubated mix=89%
 Post overnight dialysis=91%
 Particle size=127.5 nm
 Polydispersity=0.11

8 ml prep: anti-B-gal siRNA in DSPC:Chol:DODMA:PEG-DSG liposomes
 Post dilution & incubated mix=90%
 Post overnight dialysis=90%
 Post sterile-filter=90%
 Particle size=111.6 nm
 Polydispersity=0.24

Example 2

Downregulation of Intracellular Expression in Cells by Delivering In Vitro an SNALP Formulation Encapsulating siRNA This example demonstrates downregulation of #-Gal expression in CT26.CL25 cells delivered in vitro DSPC:Cholesterol:DODMA:PEG-DMG liposomes encapsulating anti-#-Gal siRNA. The results are depicted in FIG. 1.

In vitro delivery of 0.2 μg Oligofectamine-encapsulated anti-β-Gal siRNA decreased β-Gal activity by about 60% in comparison to unexposed control cells. Encapsulating 1.5 μg anti-β-Gal siRNA in DSPC:Cholesterol:DODMA:PEG-DMG liposomes decreased β-Gal activity by about 30% in comparison to unexposed control cells.

Example 3

Assays for Serum Stability

Lipid/therapeutic nucleic acid particles formulated according to the above noted techniques can be assayed for serum stability by a variety of methods.

For instance, in a typical DNase 1 digestion, 1 μg of DNA encapsulated in the particle of interest is incubated in a total volume of 100 μL of 5 mM HEPES, 150 mM NaCl, 10.0 mM $MgCl_2$ pH 7.4. DNase treated samples are treated with either 100 or 10 U of DNase I (Gibco-BRL). 1.0% Triton X-100 can be added in control experiments to ensure that lipid formulations are not directly inactivating the enzyme. Samples are incubated at 37° C. for 30 min after which time the DNA is isolated by addition of 500 μL of DNAZOL followed by 1.0 mL of ethanol. The samples are centrifuged for 30 min at 15,000 rpm in a tabletop microfuge. The supernatant is decanted and the resulting DNA pellet is washed twice with 80% ethanol and dried. This DNA is resuspended in 30 μL of TE buffer. 20 μL of this sample is loaded on a 1.0% agarose gel and subjected to electrophoresis in TAE buffer.

In a typical serum assay, 50 μg of DNA in free, encapsulated, or encapsulated+0.5% Triton X100 was aliquoted into 1.5 mL Eppendorf tubes. To the tubes were added 45 μl normal murine or human serum, dH2O (to make final volume 50 μL). The tubes were sealed with parafilm and incubated at 37° C. A sample of the free, encapsulated, or encapsulated+ 0.5% Triton X100 not digested by nuclease (standard) was frozen in liquid nitrogen in an Eppendorf tube and stored at −20° C. Aliquots were taken at various time points, added to GDP buffer containing proteinase K (133 μg/mL) and immediately frozen in liquid nitrogen to stop the reaction. Once all of the time points were collected, the samples were incubated at 55° C. in a waterbath to activate proteinase K enabling it to denature any remaining exonuclease. Proteinase K digested samples were applied to polyacrylamide gels to assess levels of exonuclease degradation.

Particles disclosed above demonstrate serum stability by showing less than 5% and preferably undetectable amounts of DNA degradation (partial or total) as a result of such treatment, even in the presence of 100 U DNase 1. This compares favorably to free DNA, which is completely degraded, and plasmid/lipid complexes (such as DOTMA or DODAC:DOPE complexes), wherein DNA is substantially (i.e., greater than 20%, often 80%) degraded after such treatment.

Example 4

Characterization of SNALPs

This example describes disease site targeting and gene expression resulting from intravenous administration of SNALP in tumor bearing mice. In this example, the encapsulated nucleic acid is a plasmid.

The SNALP method resulted in the encapsulation of plasmid DNA in small (diameter ~70 nm) "stabilized nucleic acid-lipid particles" (SNALP). SNALP consist of one plasmid per particle, encapsulated within a lipid bilayer stabilized by the presence of a bilayer stabilizing component, such as a poly(ethyleneglycol) (PEG) coating. SNALP exhibited extended circulation lifetimes following intravenous administration and promoted delivery of intact plasmid to distal tumor sites resulting in reporter gene expression at the disease site.

Figure 7:
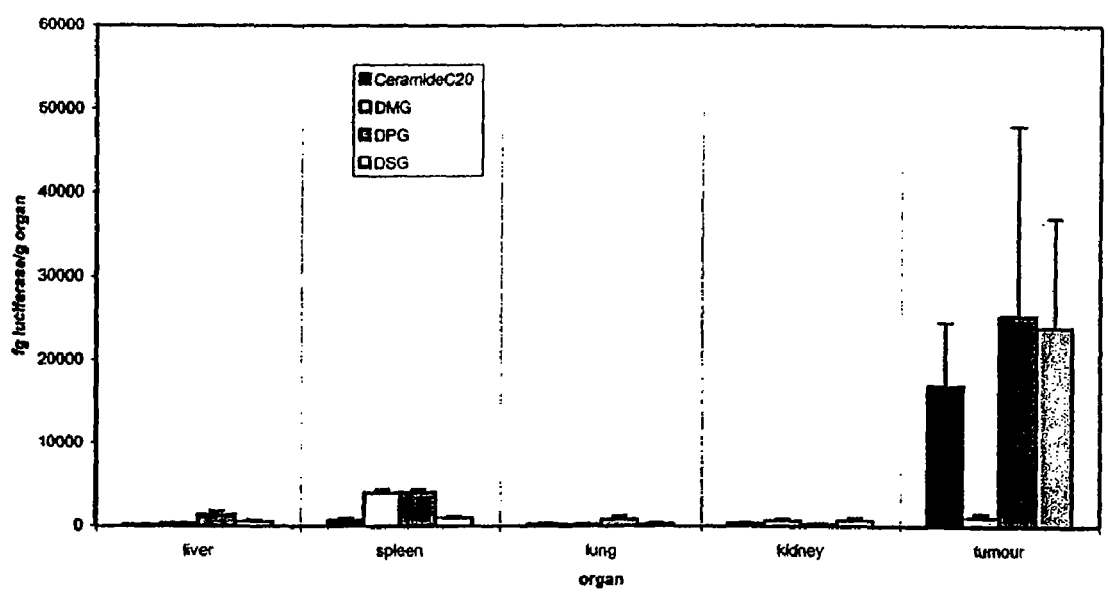
FIG. 7 illustrates the luciferase gene expression 24 hrs post IV administration of SPLPs containing PEG-CeramideC$_{20}$ versus PEG-DAGs in Neuro-2a Tumor Bearing Male A/J Mice.
Figure 8:
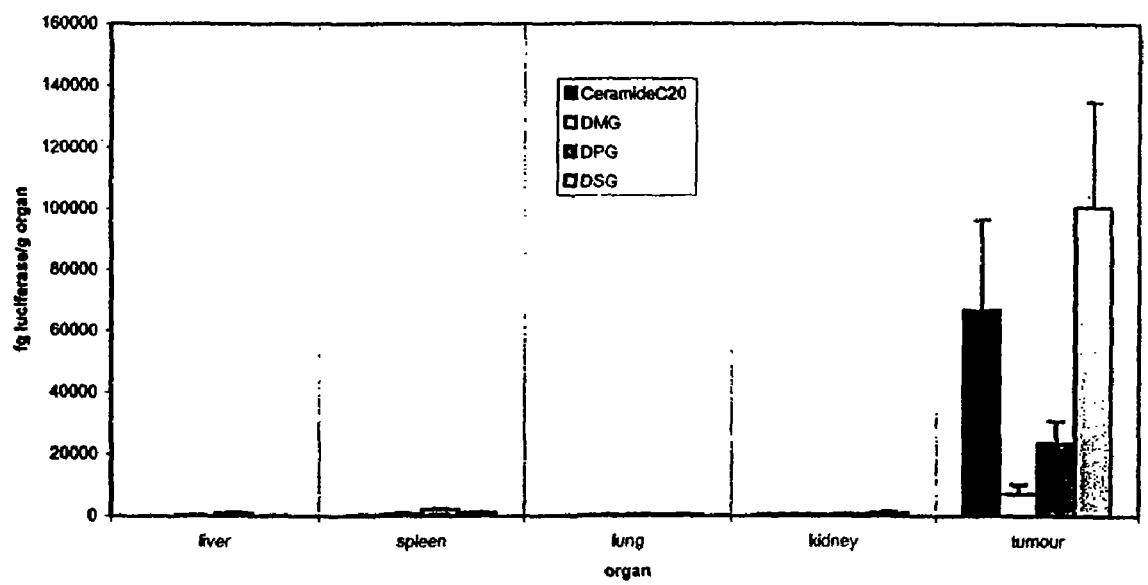
FIG. 8 illustrates the luciferase gene expression 48 hrs post IV administration of SPLPs containing PEG-CeramideC$_{20}$ versus PEG-DAGs in Neuro-2a Tumor Bearing Male A/J Mice.
Figure 9:
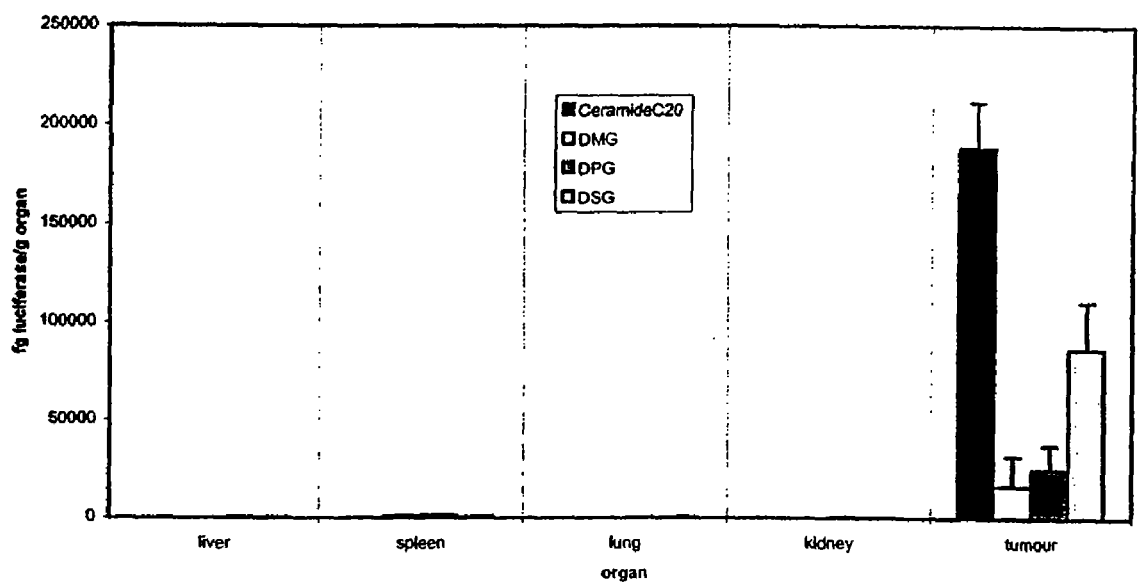
FIG. 9 illustrates the luciferase gene expression 72 hrs post IV administration of SPLPs containing PEG-CeramideC$_{20}$ versus PEG-DAGs in Neuro-2a Tumor Bearing Male A/J Mice.

SNALP with long circulation times accumulated to levels corresponding to five to ten percent of the total injected dose per gram of tumor or greater than 1000 copies of plasmid DNA per cell, giving rise to levels of gene expression that were more than two orders of magnitude greater than those observed in any other tissue. Interestingly, although the liver accumulated 20-30% of the total injected dose, very low levels of gene expression were observed in the liver. This is thought to be due to the limited hepatocellular uptake of the PEG-ylated SNALP. See, FIGS. 7-9.

The in vivo delivery and transfection potential of nucleic acid-lipid particles containing a bilayer stabilizing component was further enhanced through the incorporation of a cationic PEG lipid (CPL) consisting of a DSPE anchor, PEG$_{3400}$ spacer chain and a cationic head group. When CPL were incorporated into SNALP at concentrations of 2 to 4 mol % the resulting CPL-SNALP were of a similar size and stability as native SNALP. Incorporation of CPL resulted in a dramatic increase in intracellular delivery and a concomitant increase in transfection activity measured both in vitro and in vivo. Specifically, CPL-SNALP yielded $10^5$-fold more in vitro gene expression than native SNALP. When CPL-SNALP were administered intravenously they yielded a substantial (250 fold) increase in hepatic gene expression compared to native SNALP. The increase in CPL-SNALP potency was specific to the liver. The levels of gene expression measured in the lung, kidney, spleen or heart remained unchanged, contributing to more than two orders of magnitude differential in the gene expression measured in the liver vs. other organs.

These results illustrate the potential for modulating the delivery properties of PEG-lipid containing systems while retaining the stability and small uniform size required to achieve systemic gene delivery. In particular they demonstrate that disease site targeting and tissue specific gene expression can be re-programmed by altering the lipid composition of non-viral gene delivery systems.

Example 5

SNALPs Containing PEG-DAG Conjugates

This example demonstrates the preparation of a series of PEG-diacylglycerol lipids (PEG-DAG) SNALPs. In this example, the encapsulated nucleic acid is a plasmid.

PEG-DAG SNALP were prepared incorporating 10 mol percent PEG-dilaurylglycerol ($C_{12}$), PEG-dimyristylglycerol ($C_{14}$), PEG-dipalmitoylglycerol ($C_{16}$) or PEG-disterylglycerol ($C_{18}$) and evaluated for in vitro transfection activity, pharmacokinetics and the biodistribution of gene expression resulting from systemic administration in tumor bearing mice. PEG-DAG lipid containing SNALP demonstrated a similar relationship between acyl chain length and in vitro transfection activity to those containing PEG-ceramides. Shorter acyl chain anchors (dimyristyl ($C_{14}$) and dipalmitoyl ($C_{16}$)) resulted in SNALP particles that were less stable but have higher transfection activity in vitro than those incorporating longer acyl chain anchors (disteryl ($C_{18}$)). Evaluation of the pharmacokinetics of PEG-DAG containing SNALP confirmed a correlation between the stability of the PEG lipid component and the circulation lifetime of SNALP. SNALP containing PEG-dimyristylglycerol ($C_{14}$), PEG-dipalmitoylglycerol ($C_{16}$) and PEG-disterylglycerol ($C_{18}$) demonstrated circulation half-lives of 0.75, 7 and 15 hours respectively. Extended circulation lifetime in turn correlates with an increase in tumor delivery and concomitant gene expression.

Upon intravenous administration, PEG-disterylglycerol ($C_{18}$) containing SNALP bypass so-called 'first pass' organs, including the lung, and elicited gene expression in distal tumor tissue. The level of reporter gene expression observed in tumors represents a 100 to 1000-fold differential over that observed in any other tissue. This compared well with the behavior of SNALP containing PEG-ceramide $C_{20}$. The incorporation of PEG-DAG in SNALP confirmed that small size, low surface charge and extended circulation lifetimes are prerequisite to the passive disease site targeting leading to accumulation of plasmid DNA and gene expression in tumors following systemic administration of non-viral transfection systems. See, FIGS. 3-9.

Materials and Methods

Materials

DOPE and DSPC were obtained from Northern Lipids (Vancouver, BC). DODAC and the PEG-diacylglycerols were manufactured by Inex Pharmaceuticals (Burnaby, BC). The other materials, HEPES, OGP and $^3$H-cholesteryl hexadecyl ether, were obtained from a number of different commercial sources.

DOPE:DODAC:PEG-Diacylglycerols (82.5:7.5:10) large unilamellar vesicles were prepared via detergent dialysis in Hepes Buffered Saline (150 mM NaCl and 10 mM HEPES) for 48 hours. Lipid stock solutions were prepared in ethanol and then dried down to create a lipid film which was reconstituted in final 200 mM OGP. LUVs were labeled with $^3$H-cholesteryl hexadecyl ether at 1 uCi/1 mg lipid. Particle sizes were determined by nicomp analysis. Radioactivity was determined by scintillation counting with Picofluor20.

SNALP containing PEG-Diacyglycerols were formulated via detergent dialysis by varying the salt concentration to maximize the percent of DNA encapsulation. Optimal salt concentration was chosen for the 48 hour detergent dialysis. Empty vesicles were removed by one step sucrose centrifugation. 3.5% sucrose was used to separate out the empty particles from the plasmid-containing PEG-Diacylglycerol formulations except for PEG-Dimyristylglycerol containing SNALP which used 5.0% sucrose. Empty vesicles migrated to the top of the tube which were fractioned out and removed.

In Vitro Transfection $5 \times 10^4$ cells/ml were plated onto 24-well plates (1 ml). Cells were left to grow for 24 hours. 500 µl of transfection media (2.5 µg/well) was added and then incubated for stated timepoints. Transfection media was aspirated after timepoint and then exposed to complete media for another 24 hours at 37° C.

in 5.0% $CO_2$. Complete media was removed. Cells were washed with PBS twice and stored at −70° C. until day of experiment. Cells were lysed with 150 µl of 1×CCLR containing protease inhibitors. Plates were shaken for 5 minutes. 20 µl of each sample were assayed in duplicate on a 96-well luminescence plate for luciferase activity.

Pharmacokinetics, Biodistribution, and In Vivo Gene Expression

Pharmacokinetics and biodistribution were all determined by normalizing the data to the quantity of radioactivity present. Approximately 500 µl of blood was obtained by cardiac puncture. Red blood cells and plasma were separated by centrifugation (4° C., 3000 rpm, 10 minutes) and 100 µl of plasma was used to determine radioactive counts. Organs were harvested at specified timepoints and homogenized in lysing matrix tubes (Fast Prep, 2×15 seconds, 4.5 intensity) to assay a portion of the mixture.

Gene expression was determined by luciferase assay. Organs were harvested, homogenized, and kept on ice throughout the experiment. Lysates were centrifuged (10,000 rpm, 5 minutes) and 20 µl of supernatant were assayed in duplicate on a 96-well luminescence plate for luciferase activity. The results are depicted in FIGS. 6-9.

In Vitro Gene Silencing

Figure 17:
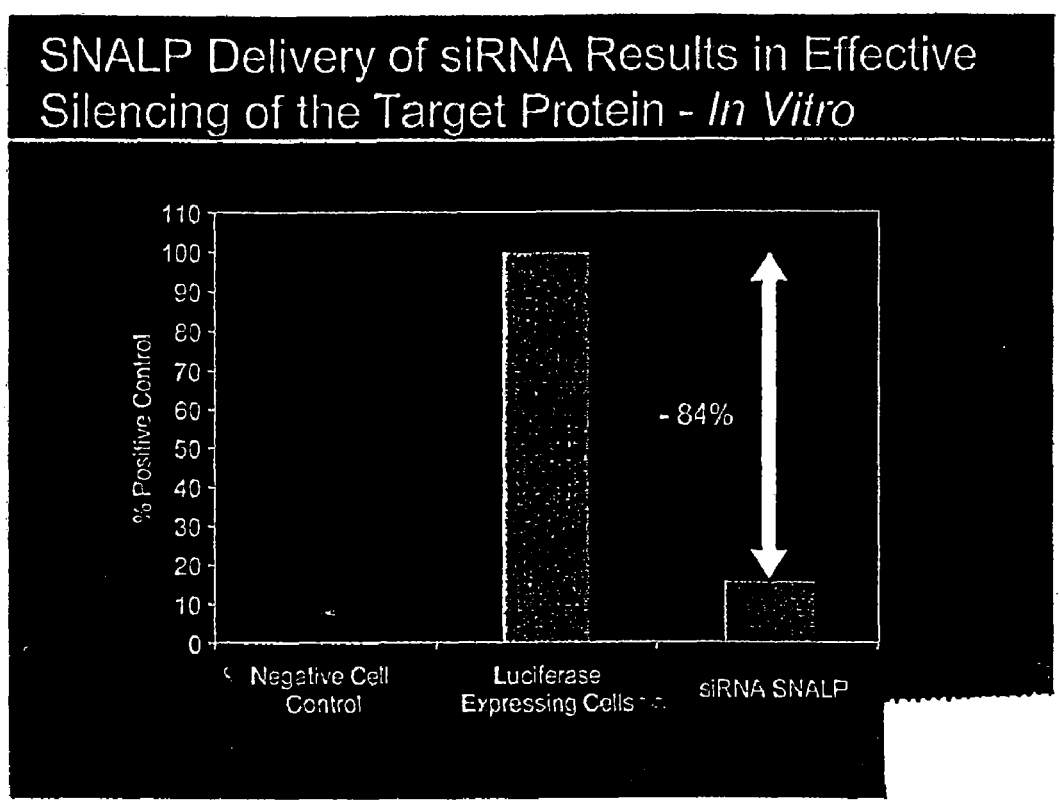
FIG. 17 illustrates in vitro data demonstrating silencing of luciferase expression in luciferase expressing cells treated with SPLPs comprising a PEG-lipid conjugate and containing a plasmid encoding luciferase under the control of the CMV promoter and SNALPs comprising a PEG-lipid conjugate conjugate and containing anti-luciferase siRNA.
Figure 18:
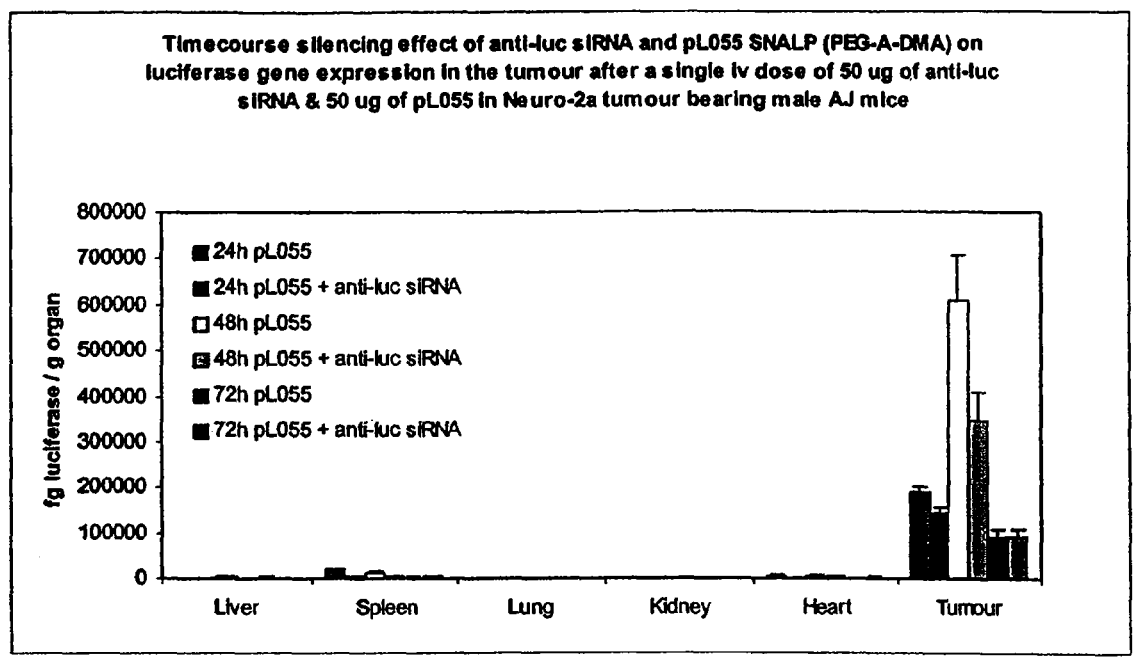
FIG. 18 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 19:
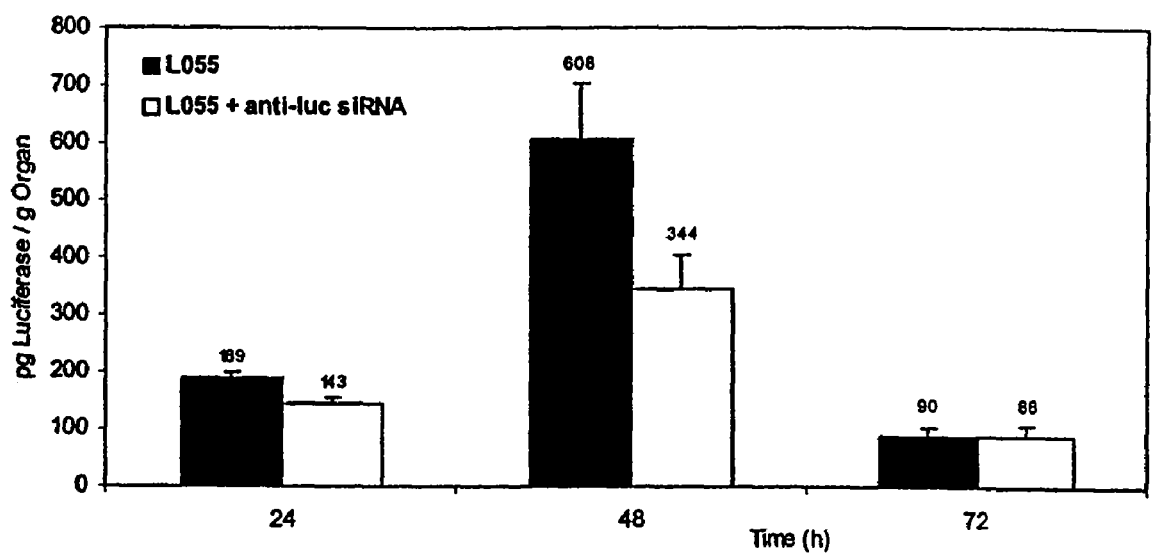
FIG. 19 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 20:
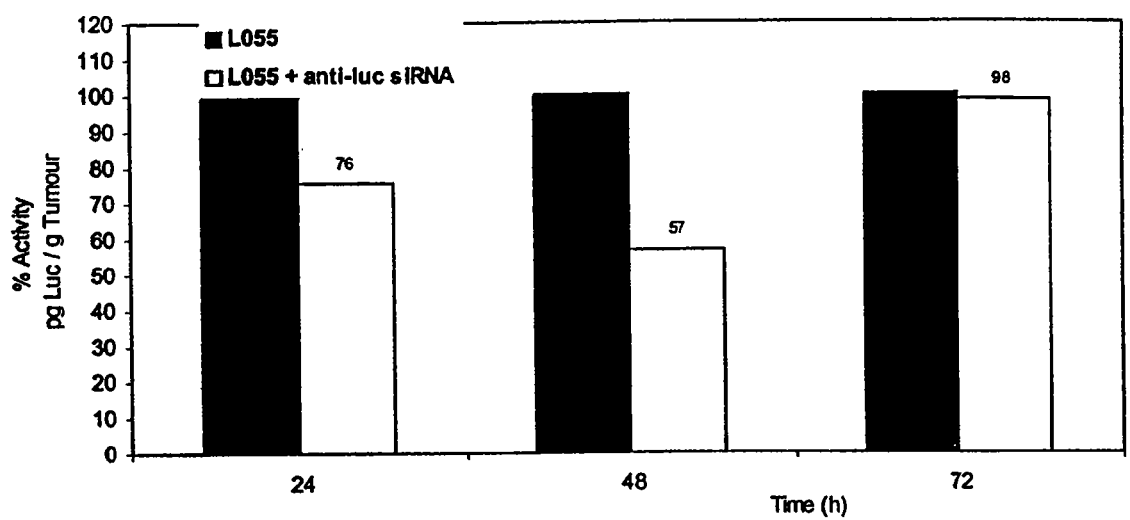
FIG. 20 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 21:
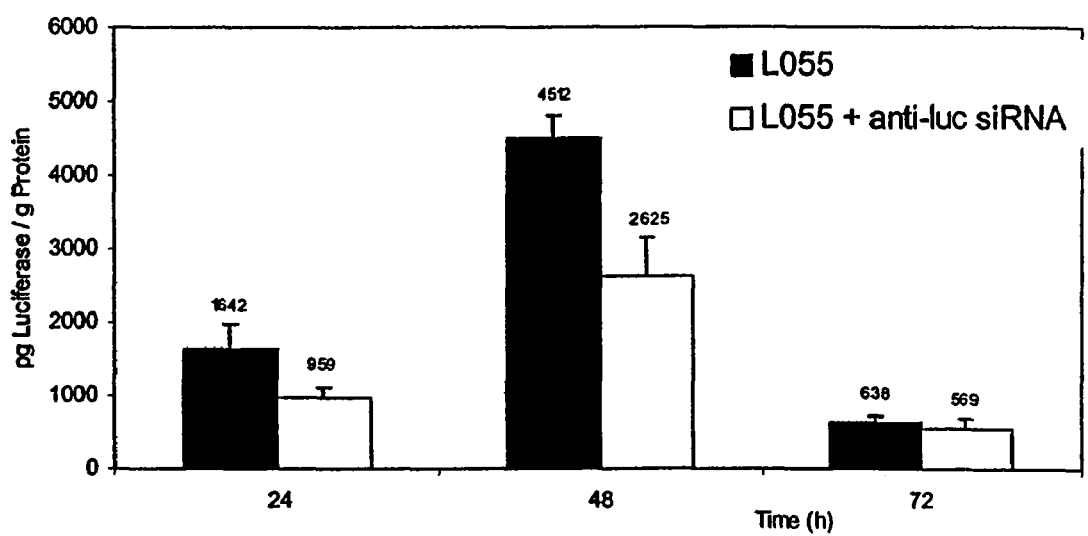
FIG. 21 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 22:
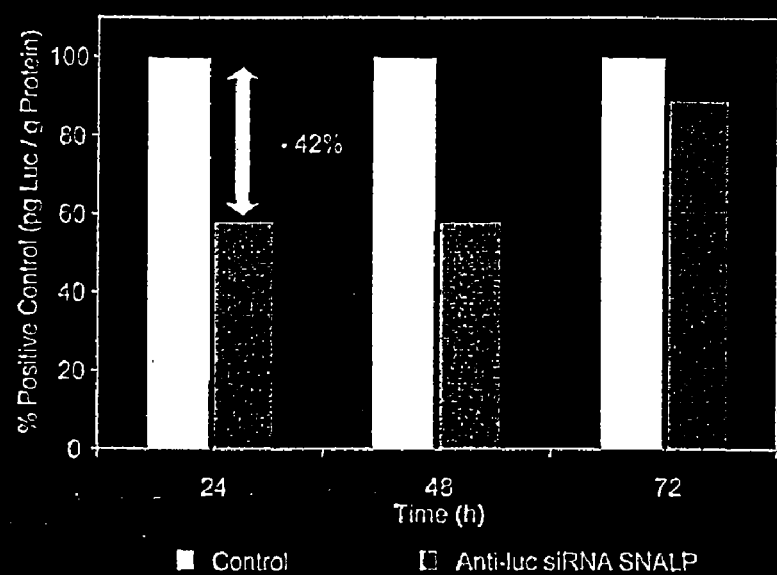
FIG. 22 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.

Cells were transfected with SPLP comprising PEG-lipid conjugates and containing a plasmid encoding luciferase under the control of the CMV promoter and SNALPs containing anti-luciferase siRNA, according to the methods described above. Gene expression was determined by luciferase assay. The results are depicted in FIG. 17.

Example 6

Expression of Nucleic Acids Encapsulated in SPLP Comprising PEG-dialkyloxypropyl Conjugates This examples describes experiments comparing expression of nucleic acids encapsulated in SPLP comprising PEG-dialkyloxypropyl conjugates. All SPLP formulations comprise a plasmid encoding luiferase under the control of the CMV promoter (pLO55)

| Group | # Mice | Tumor | Route | Treatment | Route | # Doses | Timepoint | ASSAY |
|---|---|---|---|---|---|---|---|---|
| A | 4 | Neuro-2a | SC | PBS | IV | 1 | 48 hrs | Body weights, Blood analyses, Luciferase activity |
| B | 5 | Neuro-2a | SC | SPLP PEG-DSG | IV | 1 | 48 hrs | |
| C | 5 | Neuro-2a | SC | SPLP PEG-A-DSA | IV | 1 | 48 hrs | |
| D | 5 | Neuro-2a | SC | SPLP PEG-A-DPA | IV | 1 | 48 hrs | |
| E | 5 | Neuro-2a | SC | SPLP PEG-A-DMA | IV | 1 | 48 hrs | |

The lipids (DSPC:CHOL:DODMA:PEG-Lipid) were present in the SPLP in the following molar ratios (20:55:15:10). The following formulations were made:

| Group | # Mice | Seeding date | Treatment | Injection date | Collection date |
|---|---|---|---|---|---|
| A | 4 | Day 0 | PBS | Day 12 | Day 14 |
| B | 5 | Day 0 | SPLP PEG-DSG | Day 12 | Day 14 |
| C | 5 | Day 0 | SPLP PEG-A-DSA | Day 12 | Day 14 |
| D | 5 | Day 0 | SPLP PEG-A-DPA | Day 12 | Day 14 |
| E | 5 | Day 0 | SPLP PEG-A-DMA | Day 12 | Day 14 |

A: PBS sterile filtered, 5 mL.
B: pL055-SPLP with PEG-DSG, 2 mL at 0.50 mg/mL.
C: pL055-SPLP with PEG-A-DSA, 2 mL at 0.50 mg/mL.
D: pL055-SPLP with PEG-A-DPA, 2 mL at 0.50 mg/mL.
E: pL055-SPLP with PEG-A-DMA, 2 mL at 0.50 mg/mL.

$1.5 \times 10^6$ Neuro2A cells were administered to each mouse on day 0. When the tumors were of a suitable size (200-400 $mm^3$), mice were randomized and treated with one dose of an SPLP formulation or PBS by intravenous (IV) injection. Dose amounts are based on body weight measurements taken on the day of dosing. 48 hours after SPLP administration, the mice were sacrificed, their blood was collected, and the following tissues were collected weighed, immediately frozen and stored at −80 C until further analysis: tumor, liver (cut in 2 halves), lungs, spleen & heart.

Figure 11:
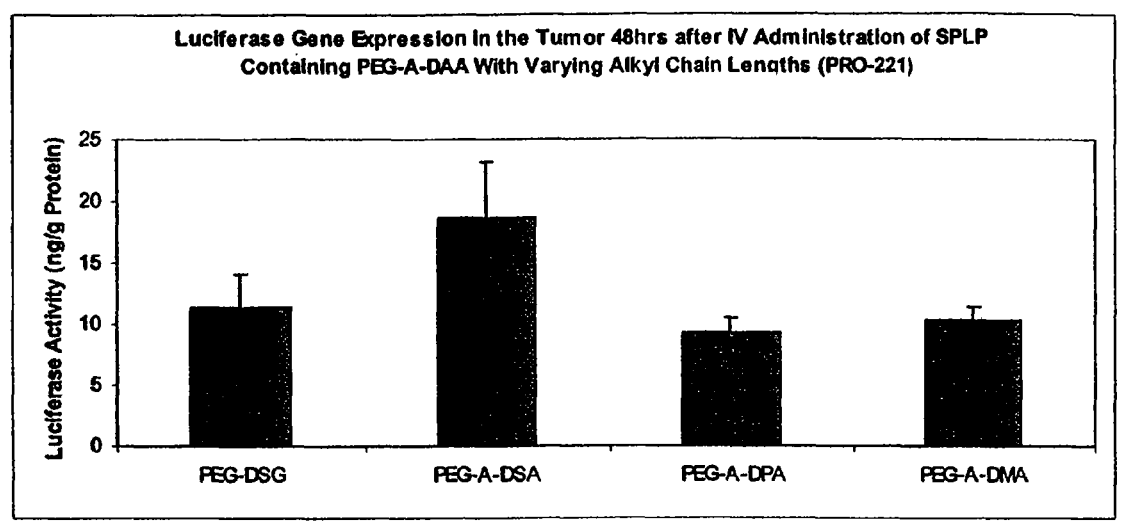
FIG. 11 illustrates data showing luciferase gene expression in tumors 48 hours after intravenous administration of SPLP comprising PEG-DAA conjugates and PEG-DAG conjugates.
Figure 12:
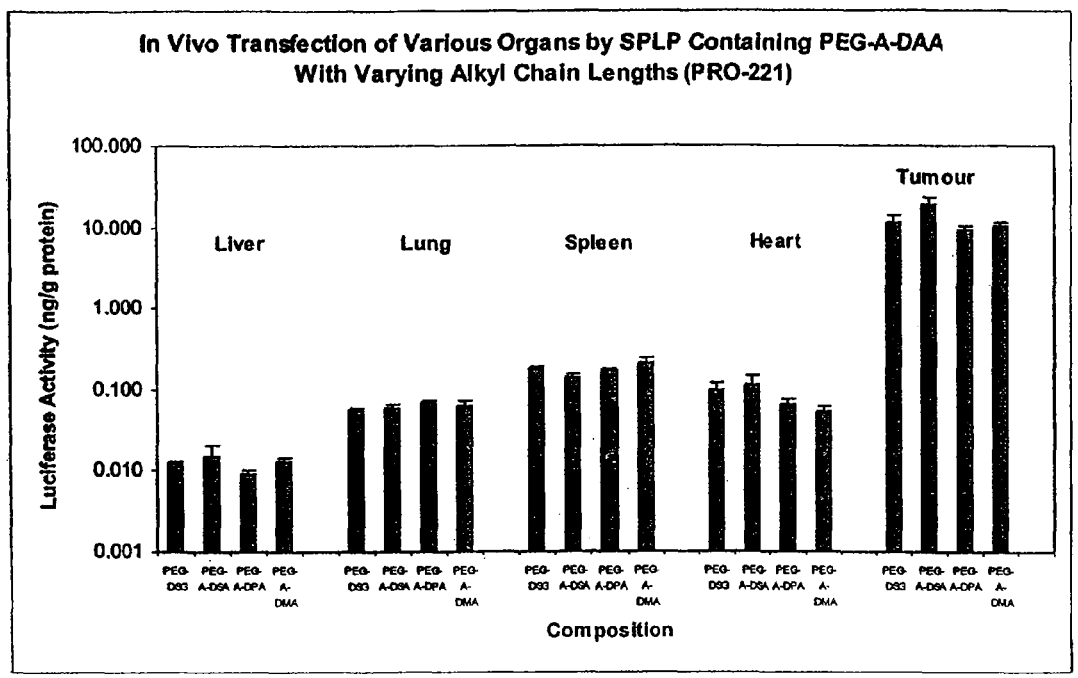
FIG. 12 illustrates data showing luciferase gene expression in liver, lung, spleen, heart, and tumor following intravenous administration of SPLP comprising PEG-DAA conjugates and PEG-DAG conjugates.
Figure 13:
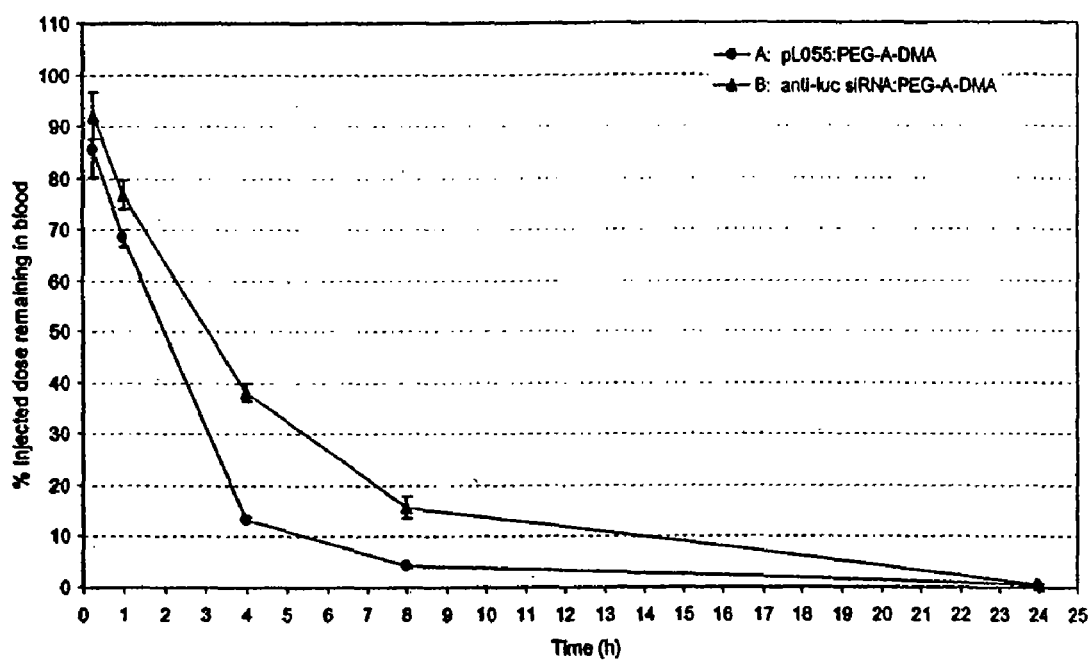
FIG. 13 illustrates data from clearance studies in Neuro-2a tumor bearing male A/J mice after administration of SPLPs comprising a PEG-DAA conjugate and containing a plasmid encoding luciferase under the control of the CMV promoter and SNALPs comprising a PEG-DAA conjugate and containing anti-luciferase siRNA.
Figure 14:
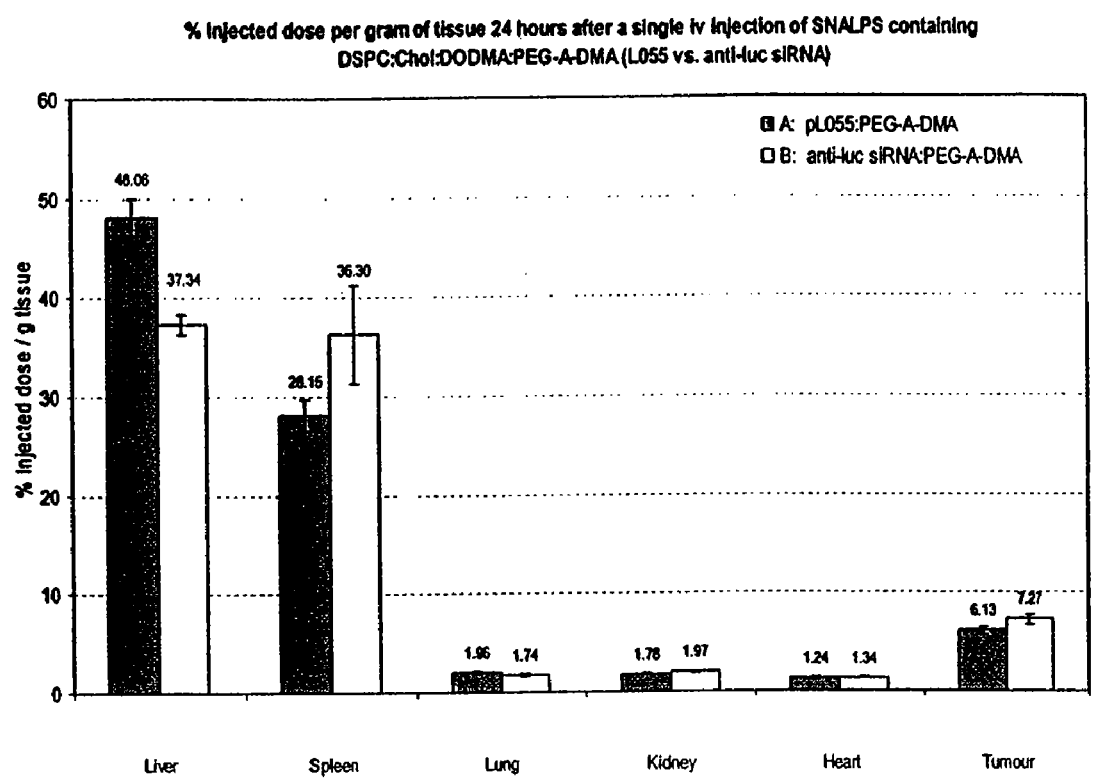
FIG. 14 illustrates data from studies of the pharmacokinetic properties of SPLPs comprising a PEG-DAA conjugate and containing a plasmid encoding luciferase under the control of the CMV promoter and SNALPs comprising a PEG-DAA conjugate and containing anti-luciferase siRNA in Neuro-2a tumor bearing male A/J mice.
Figure 15:
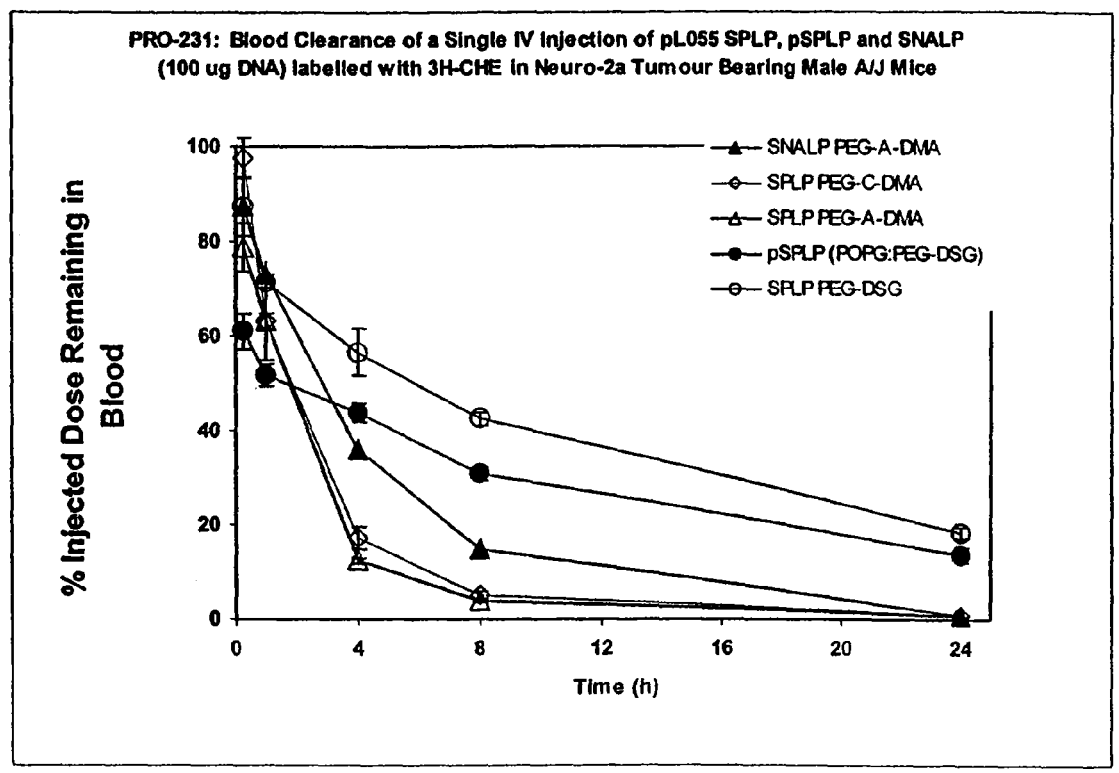
FIG. 15 illustrates data from clearance studies in Neuro-2a tumor bearing male A/J mice after administration of SPLPs comprising a PEG-DAA conjugate or a PEG-DAG conjugate and containing a plasmid encoding luciferase under the control of the CMV promoter, pSPLPs comprising a PEG-DAG conjugate and containing a plasmid encoding luciferase under the control of the CMV promoter and SNALPs comprising a PEG-DAA conjugate and containing anti-luciferase siRNA.
Figure 16:
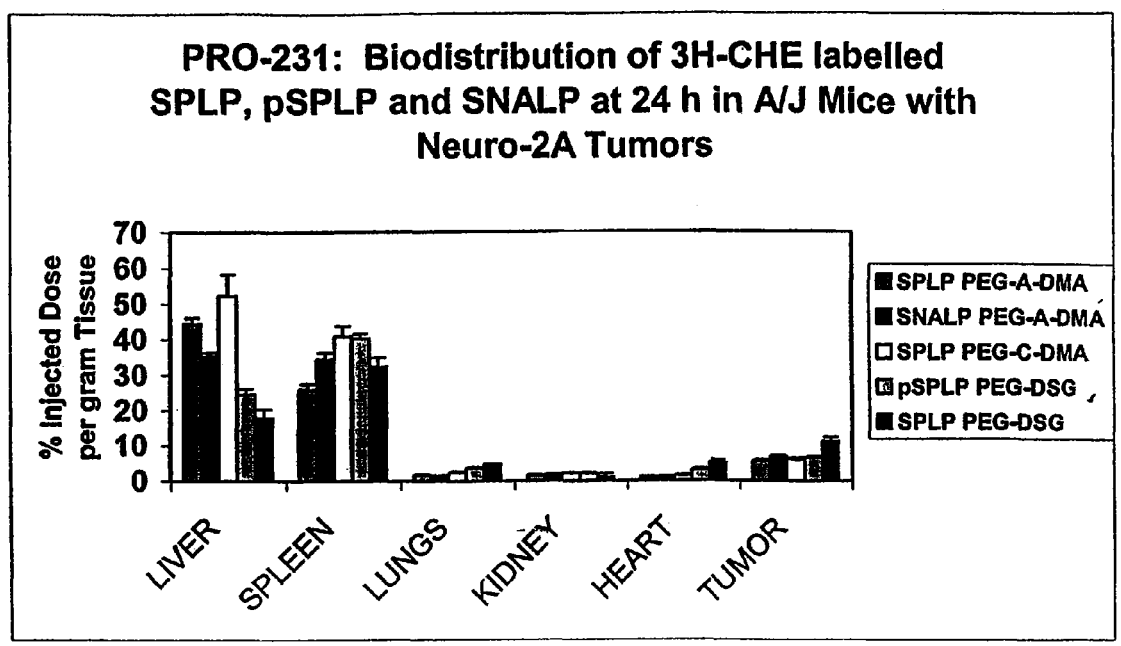
FIG. 16 illustrates data from studies of the pharmacokinetic properties of SPLPs comprising a PEG-DAA conjugate or a PEG-DAG conjugate and containing a plasmid encoding luciferase under the control of the CMV promoter, pSPLPs comprising a PEG-DAG conjugate and containing a plasmid encoding luciferase under the control of the CMV promoter and SNALPs comprising a PEG-DAA conjugate and containing anti-luciferase siRNA in Neuro-2a tumor bearing male A/J mice.

Gene expression in collected tissues was determined by assaying for enzymatic activity of expressed luciferase reporter protein. The results are shown in FIGS. 11 and 12.

The results indicate that SPLP comprising PEG-dialkyloxypropyls (i.e., PEG-DAA) can conveniently be used to transfect distal tumor to substantially the same extent as SPLP comprising PEG-diacylglycerols. Moreover, the transfection levels seen with SPLP containing PEG-dialkyloxypropyl are similar to those seen with SPLP containing PEG-diacylglycerols (e.g. PEG-DSG). It was also shown that similar to the PEG-diacylglycerol system, very little transfection occurred in non-tumor tissues. Moreover, the SPLP comprising PEG-dialkyloxypropyls exhibit reduced toxicity compared to other SPLP formulations.

Example 7

SNALPs Containing PEG-dialkyloxypropyl Conjugates

This example described experiments analyzing the biodistribution (local and systemic) and pharmacokinetics of a series of PEG-dialkyloxypropyl lipids SNALPs (i.e., SPLP containing encapsulated siRNA.

Local Biodistribution

To determine the local distribution of SPLP resulting from systemic administration of anti-β galactosidase siRNA containing SNALP in Neuro-2a tumor bearing mice via fluorescent microscopy.

A: PBS

B: anti-βgal siRNA-Rhodamine-PE labeled-DSPC:Chol:DODMA:PEG-A-DMA SNALP (1:20:54:15:10)

| Group | Mice | Cells | Treatment | Timepoint | Assay |
|---|---|---|---|---|---|
| A | 2 | Neuro2A | PBS | 24 hr | Fluorescent Photomicroscopy |
| B | 5 | Neuro2A | anti-Bgal siRNA-Rhodamine-PE labeled-DSPC:Chol:DODMA:PEG-A-DMA | 24 hr | Fluorescent Photomicroscopy |

A: PBS
B: anti-βgal siRNA-Rhodamine-PE labeled-DSPC:Chol:DODMA:PEG-A-DMA SNALP (1:20:54:15:10)

$1.5 \times 10^6$ Neuro2A cells were administered to each mouse on day 0. When the tumors were of a suitable size (200-400 mm$^3$, typically day 9-12)), mice were randomized and treated with one dose of an SNALP formulation comprising 100 μg siRNA or PBS by intravenous (IV) injection in a total volume of 230 μl. Dose amounts are based on body weight measurements taken on the day of dosing. 24 hours after SPLP administration, the mice were sacrificed, their blood was collected, and the following tissues were collected weighed, immediately frozen and stored at −80 C until further analysis: tumor, liver (cut in 2 halves), lungs, spleen & heart.

Local distribution of the SNALP was determined by fluorescence microscopy. Accumulation of SNALP is seen in, e.g., the liver, demonstrating the SNALP comprising PEG-dialkyloxypropyls are able to extravasate, i.e., exit the circulation and home to a target tissue or organ.

Pharmacokinetics and Systemic Biodistribution

This example illustrates the pharmacokinetics and biodistribution of SPLPs containing a plasmid encoding luciferase under the control of the CMV promoter (L055) and SNALPs containing anti-luciferase siRNA in mice seeded subcutaneously with Neuro2A tumors.

| Group | Mice | Cells | Treatment | Timepoint(h) |
|---|---|---|---|---|
| A | 6 | Neuro2A | [3-H]CHE-L055-DSPC:Chol:DODMA:PEG-A-DMA | 0.25, 1, 4, 8, 24 |
| B | 6 | Neuro2A | [3-H]CHE-anti-luc siRNA-DSPC:Chol:DODMA:PEG-A-DMA | 0.25, 1, 4, 8, 24 |
| C | 6 | Neuro2A | [3-H]CHE-L055-DSPC:Chol:DODMA:PEG-C-DMA | 0.25, 1, 4, 8, 24 |
| D | 6 | Neuro2A | [3-H]CHE-L055-pSPLP (PEI) | 0.25, 1, 4, 8, 24 |
| E | 6 | Neuro2A | [3-H]CHE-L055-DSPC:Chol:DODMA:PEG-DSG | 0.25, 1, 4, 8, 24 |

All samples are to be provided at 0.5 mg/ml nucleic acid. The following SPLP and SNALP formulations were prepared:

| Group | # Mice | Seeding date | Treatment | Injection date | Collection date |
|---|---|---|---|---|---|
| A | 6 | Day 0 | [3-H]CHE-L055-DSPC:Chol:DODMA:PEG-A-DMA | Day 12 | July 31 |
| B | 6 | Day 0 | [3-H]CHE-anti-luc siRNA-DSPC:Chol:DODMA:PEG-A-DMA | Day 12 | July 31 |
| C | 6 | Day 0 | [3-H]CHE-L055-DSPC:Chol:DODMA:PEG-C-DMA | Day 13 | Day 14 |

-continued

| Group | # Mice | Seeding date | Treatment | Injection date | Collection date |
|---|---|---|---|---|---|
| D | 6 | Day 0 | [3-H]CHE-L055-pSPLP (PEI) | Day 13 | Day 14 |
| E | 6 | Day 0 | [3-H]CHE-L055-DSPC:Chol:DODMA:PEG-DSG | Day 14 | Day 15 |

A: [$^3$H] CHE-L055-DSPC:Chol:DODMA:PEG-A-DMA (20:55:15:10)
B: [$^3$H] CHE-anti-luc siRNA-DSPC:Chol:DODMA:PEG-A-DMA (20:55:15:10)
C: [$^3$H] CHE-L055-DSPC:Chol:DODMA:PEG-C-DMA (20:55:15:10)
D: [$^3$H] CHE-L055-pSPLP (PEI) (i.e., precondensed SPLP)
E: [$^3$H] CHE-L055-DSPC:Chol:DODMA:PEG-DSG (20:55:15:10)

30 male A/J mice (Jackson Laboratories) were seeded subcutaneously with Neuro 2A cells at a dose of $1.5 \times 10^6$ cells in a total volume of 50 µL phosphate buffered saline on day zero. After tumors reached appropriate size (typically on day 9 or later), 200 µl (100 µg nucleic acid) of the SPLP or SNALP preparations described above, were administered intravenously. 0.25, 1, 2, 4, and 8 hours after administration of SPLP or SNALP, mice were weighed and blood (typically 25 µL) was collected by tail nick. 24 hours after administration of SPLP or SNALP, mice were sacrificed, blood was collected and assayed for clearance of [$^3$H]CHE. Organs (e.g., liver, lung, spleen, kidney, heart) and tumors were collected and evaluated for [$^3$H]CHE accumulation. The results are shown in FIGS. 13-16.

For all formulations, SPLP containing PEG-DSG remained in circulation the longest, with 50% of the injected dose remaining after 6 h. Interestingly, there appeared to be a initial rapid clearance of pSPLP within the first 15 minutes that was not seen for any other formulation. After 1 h the clearance profile of the pSPLP was quite similar to SPLP. This initial rapid clearance for the pSPLP sample may indicate that there are actually two types of particles present, one that clears very rapidly and one that behaves very much like SPLP.

Anti-Luc siRNA containing vesicles (SNALP) formulated with the C14 PEG-A-DMA showed more rapid clearance from blood than SPLP containing the C18 PEG-DSG. However, this SNALP formulation showed significantly slower blood clearance than SPLP formulated with the same PEG lipid. A possible reason for this result maybe that siRNA containing particles can evade the cellular immune system more readily than plasmid containing SPLP.

SPLP comprising PEG-C-DMA demonstrated a rapid clearance from blood, which was substantially the same as that observed for SPLP comprisig PEG-A-DMA. For both of these formulations, the plasma half lives were approximately 2 h, lower than for SPLP containing C18 PEG-lipids.

SPLP containing PEG-DSG had the highest tumor accumulation at 10.9% inject dose per gram tissue. The two SPLP formulations containing the C14 PEG-lipids, PEG-A-DMA and PEG-C-DMA, had much lower tumor accumulation of 6.1% and 5.9% injected dose per gram tissue. The SiRNA SNALP had slightly more tumor accumulation than an SPLP sample with the same PEG-lipid at 7.3%, which also correlates relatively well with the plasma half-life for this SNALP. The pSPLP formulation had tumor accumulation at 7.5%, which is lower than the comparable PEG-DSG SPLP.

Accumulation of PEG-DSG containing SPLP and pSPLP in the heart and lungs was higher than the other SPLP and SNALP, which is consistent with the increased circulation half lives of particles with C18 PEG-lipids. Not surprisingly, there was an inverse relationship between plasma half-life and accumulation in the liver for all samples tested, while no trend was apparent for sample accumulation in the spleen. Accumulation in the kidneys was very low for all formulations tested, with accumulation between 1.2 and 2.4% injected dose per gram tissue.

Example 8

Silencing of Gene Expression with SNALPS

This example illustrates silencing of gene expression in Neuro 2A tumor bearing mice after co-administration of SPLPs containing a plasmid encoding luciferase under the control of the CMV promoter and SNALPs containing anti-luciferase siRNA.

| Group | # Mice | Tumor | Route | Treatment | Timepoint | Route | # Doses |
|---|---|---|---|---|---|---|---|
| 1 | 3 | Neuro-2a | SQ | PBS/PBS | 48 h | IV | 1 |
| 24A | 4 | | | L055-SPLP/PBS mix | 24 h | | |
| 24B | 4 | | | L055-SPLP/anti-luc siRNA liposomes mix | | | |
| 48A | 4 | | | L055-SPLP/PBS mix | 48 h | | |
| 48B | 4 | | | L055-SPLP/anti-luc siRNA liposomes mix | | | |
| 72A | 4 | | | L055-SPLP/PBS mix | 72 h | | |
| 72B | 4 | | | L055-SPLP/anti-luc siRNA liposomes mix | | | |

| Group | # Mice | Seeding Date | Route | TV Treatment | Timepoint | Injection date | Collection Date |
|---|---|---|---|---|---|---|---|
| 1 | 3 | Day 0 | SQ | PBS/PBS | 48 h | Day 13 | Day 15 |
| 24A | 4 | | | L055-SPLP/PBS mix | 24 h | Day 14 | |
| 24B | 4 | | | L055-SPLP/anti-luc siRNA liposomes mix | | Day 14 | |
| 48A | 4 | | | L055-SPLP/PBS mix | 48 h | Day 13 | |
| 48B | 4 | | | L055-SPLP/anti-luc siRNA liposomes mix | | Day 13 | |
| 72A | 4 | | | L055-SPLP/PBS mix | 72 h | Day 12 | |
| 72B | 4 | | | L055-SPLP/anti-luc siRNA liposomes mix | | Day 12 | |

36 male A/J mice (Jackson Laboratories) were seeded subcutaneously with Neuro 2A cells at a dose of 1.5×10$^6$ cells in a total volume of 50 μL phosphate buffered saline on day zero. Once tumors reached appropriate size (typically on day 9 or later), 200-240 μl PBS, SPLP, or SNALP formulations (100 μg nucleic acid total) prepared as described in Example 6 above, were administered intravenously. 24, 48, or 72 after administration of PBS, SPLP or a mixture of SPLP and SNALP, mice were sacrificed and organs (e.g., liver, lung, spleen, kidney, heart) and tumors were collected and evaluated for luciferase activity. The results are shown in FIGS. 18-22.

The results demonstrate that co-administration of pLO55 SPLP and anti-luc siRNA SNALP (both containing PEG-A-DMA) maximally decreases luciferase gene expression by 40% forty-eight hours after a single iv dose.

Example 9

Synthesis of PEG-Dialkyloxypropyls (PEG-DAA's)

The following example illustrates the synthesis of three PEG-lipids, PEG-A-DMA (7), PEG-C-DMA (8), and PEG-S-DMA (9). They have a common precursor, the amine lipid 1,2-dimyristyloxypropylamine (5). This lipid has alkyl chains 14 carbon units ($C_{14}$) in length. Other PEG DAAs suitable for use in the present invention can be synthesized using similar protocols. For instance, PEG-A-DSA and PEG-C-DSA can be synthesized by using the $C_{18}$ analogue of (5). The $C_{18}$ analogue can be synthesized by simply substituting an equimolar amount of stearyl bromide for myristyl bromide in the very first step (synthesis of compound (1)).

1. Preparation of 1,2-Dimyristyloxy-3-allyloxypropane (1)

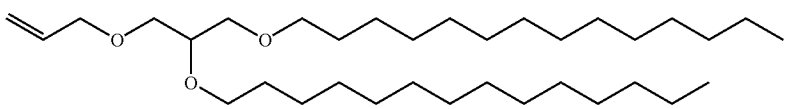

Benzene (250 ml) was added to 95% sodium hydride (11.4 g, 450.0 mmol), and the flask was flushed with nitrogen and sealed. A solution of 3-allyloxy-1,2-propanediol (6.6 g, 50.0 mmol) in benzene (75 ml) was added to the flask. Using a syringe, 97% 1-bromotetradecane (36.7 ml, 120.0 mmol) was added to the flask and the reaction was left to reflux overnight under a constant stream of nitrogen. Once cooled to room temperature, the excess sodium hydride was slowly quenched with ethanol until no further effervescence was observed. The solution was transferred to a separatory funnel with benzene (250 ml) and washed with distilled water (3×200 ml). The organic layer was dried with magnesium sulfate and the solvent removed on the rotary evaporator to yield a colourless oil. TLC (5% ether-hexane, developed in Molybdate) indicated that most of the starting material had reacted to form product. This resulting product was further purified by flash column chromatography (1-5% ether-hexane) to yield 15.0 g (57.3%) of 1,2-dimyristyloxy-3-allyloxypropane 1.

2. Preparation of 1,2-Dimyristyloxypropan-3-ol (2)

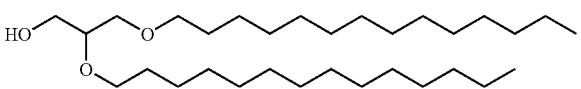

1,2-Dimyristyloxy-3-allyloxypropane 1 (15.0 g, 28.6 mmol) was dissolved in ethanol (250 ml). Trifluoroacetic acid (20 ml) was added, followed by tetrakis(triphenylphosphine) palladium(0) (4.5 g, 3.9 mmol). The flask was wrapped in tin foil and flushed with nitrogen to reduce exposure to light and air, then left to stir at 80° C. overnight. The ethanol was removed on the rotary evaporator. TLC (100% CHCl$_3$, developed in Molybdate) indicated that most of the starting material had reacted to form product. This resulting product was further purified by flash column chromatography (100% DCM) to yield 11.5 g (83.1%) 1,2-dimyristyloxypropan-3-ol 2.

3. Preparation of O-(2,3-Dimyristyloxypropyl)methanesulphonate (3)

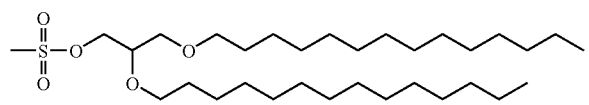

A flask containing 97% methanesulphonic anhydride (8.4 g, 48.0 mmol) was flushed with nitrogen and dissolved in anhydrous dichloromethane (50 ml). Anhydrous pyridine (3.9 ml, 48.0 mmol) was slowly added, forming a white precipitate. A solution of 1,2-dimyristyloxypropan-3-ol 15 (11.5 g, 24.0 mmol) in anhydrous dichloromethane (100 ml) was added and the reaction was left to stir overnight at room temperature. The solution was transferred to a separatory funnel with dichloromethane (100 ml) and was washed with distilled water (3×100 ml). The combined aqueous washes were then back-extracted with dichloromethane (100 ml). The combined organic layers were dried with magnesium sulfate and the dichloromethane was removed on the rotary evaporator to yield a colourless oil. TLC (100% $CHCl_3$, developed in Molybdate) indicated that the starting material had all reacted to form product. This reaction yielded 11.9 g of crude O-(2,3-dimyristyloxypropyl)methanesulphonate 3.

4. Preparation of N-(2,3-Dimyristyloxypropyl)phthalimide (4)

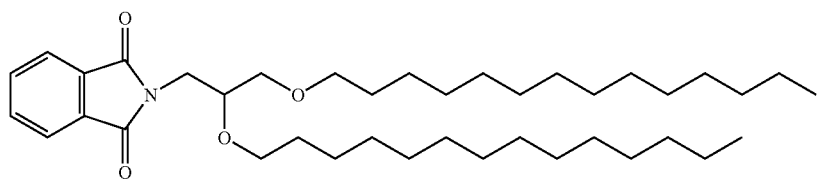

Crude O-(2,3-dimyristyloxypropyl)methanesulphonate 3 (14.2 g, 25.3 mmol) and potassium phthalimide (13.9 g, 75.0 mmol) were flushed with nitrogen and dissolved in anhydrous N,N-dimethylformamide (250 ml). The reaction was left to stir at 70° C. overnight under a constant stream of nitrogen. The N,N-dimethylformamide was removed on the rotary evaporator using a high vacuum pump instead of the usual aspirator. The residue was dissolved in chloroform (300 ml) and transferred to a separatory funnel with a chloroform rinse (50 ml), then washed with distilled water and ethanol (3×300 ml distilled water, 50 ml ethanol). The combined aqueous washes were back-extracted with chloroform (2×100 ml). The combined organic layers were dried with magnesium sulfate and the chloroform was removed on the rotary evaporator. TLC (30% ether-hexane, developed in Molybdate) indicated that the starting material had reacted to form product. This reaction yielded 13.5 g of crude N-(2,3-dimyristyloxypropyl)phthalimide 4.

5. Preparation of 1,2-Dimyristyloxypropylamine (5)

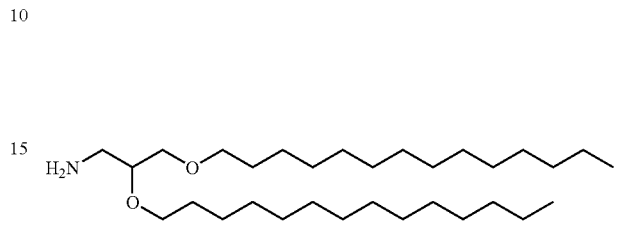

Crude N-(2,3-dimyristyloxypropyl)phthalimide 4 (20.0 g, 25.0 mmol) was dissolved in ethanol (300 ml). Hydrazine monohydrate (20 ml, 412.3 mmol) was added and the reaction was left to reflux overnight. The ethanol was removed on the rotary evaporator and the residue was redissolved in chloroform (200 ml). The precipitate was filtered off and the chloroform was removed on the rotary evaporator. TLC (10% $MeOH$—$CHCl_3$, developed in Molybdate) indicated that most of the starting material had reacted to form product. This resulting product was further purified by flash column chromatography (0-5% $MeOH$—$CHCl_3$) to yield 10.4 g (89.7% over three steps from 1,2-dimyristyloxypropan-3-ol 2) of 1,2-dimyristyloxypropylamine 5.

6. Preparation of Methoxy $PEG_{2000}$ acetic acid (6)

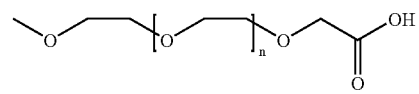

A 10% solution of concentrated sulfuric acid (20 ml) in water (180 ml) was added to sodium dichromate (3.0 g, 10 mmol). PEG$_{2000}$ methyl ether (20.0 g, 10 mmol) was dissolved in this bright orange solution and the reaction was left to stir at room temperature overnight. The product was then extracted with chloroform (3×250 ml) leaving the dark blue colour in the aqueous layer. The chloroform solvent was removed on the rotary evaporator, resulting in a pale blue wax. TLC (13% MeOH—CHCl$_3$, developed in iodine) indicated that most of the starting material had reacted to form product. This crude material was then further purified by flash column chromatography (0-15% MeOH—CHCl$_3$). The resulting product was then crystallized in ether to yield 5.6 g (27.1%) of methoxy PEG$_{2000}$ acetic acid 6 as a white solid.

7. Preparation of N-(2,3-dimyristyloxypropyl)amide PEG$_{2000}$ methyl ether (7)

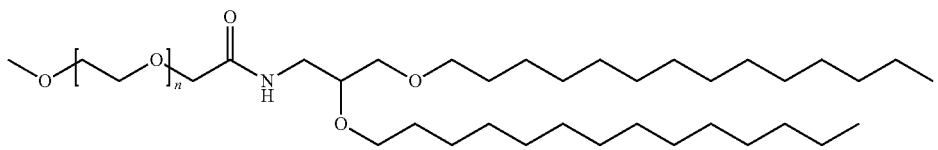

For preparation of N-(2,3-dimyristyloxypropyl)amide PEG$_{2000}$ methyl ether (i.e., PEG-A-DMA), methoxy PEG$_{2000}$ acetic acid 6 (3.4 g, 1.7 mmol) was dissolved in benzene (40 ml) and flushed with nitrogen. Oxalyl chloride (1.7 ml, 2.5 g, 20 mmol) was slowly added by a syringe and needle through the subaseal. This reaction was left to stir for 2 hours then the benzene solvent was removed on the rotary evaporator. 2,3-myristylyloxypropylamine 5 (0.87 g, 1.8 mmol) was added to the flask, followed by anhydrous dichloromethane (40 ml) and triethylamine (1.5 ml, 10 mmol). The reaction was left to stir for 48 hours. Distilled water (250 ml) was added, the solution was acidified with hydrochloric acid (1.5 ml) and shaken, and the organic layer was collected. The product was extracted from the aqueous layer with chloroform (2×65 ml). The combined organic layers were dried with magnesium sulfate. The chloroform was removed on the rotary evaporator to yield a yellow solid. TLC (10% MeOH—CHCl$_3$, developed in copper sulphate and iodine) indicated that most of the starting material had reacted to form product. This crude material was further purified by flash column chromatography (0-7% MeOH—CHCl$_3$). It was then decolourized by adding activated charcoal (2 g) and ethanol (100 ml) and allowing the mixture to rotate at 55° C. on the rotary evaporator for 30 minutes. The charcoal was filtered off and the ethanol was removed on the rotary evaporator. The product was lyophilized to yield 1.7 g (38.1%) of N-(2,3-dimyristyloxypropyl)amide PEG$_{2000}$ methyl ether 7 as a fluffy white powder.

8. Preparation of N-(2,3-dimyristyloxypropyl) carbamate PEG$_{2000}$ methyl ether (8)

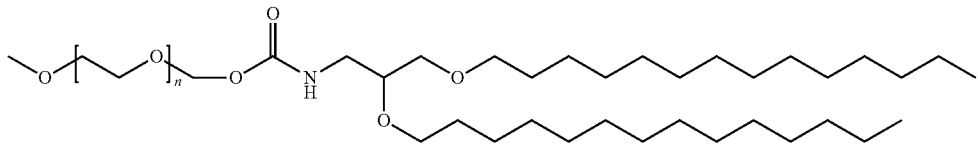

For preparation of N-(2,3-dimyristyloxypropyl) carbamate PEG$_{2000}$ methyl ether (i.e., PEG-C-DMA), steps 1-5 described above were followed. Then PEG$_{2000}$ methyl ether (2.0 g, 1.0 mmol) was flushed with nitrogen and dissolved in anhydrous dichloromethane (15 ml). Diphosgene (300 µl, 2.5 mmol) was added and the reaction was left to stir at room temperature for 3 hours. The dichloromethane was removed on the rotary evaporator and any remaining diphosgene was removed using the high vacuum pump. The flask was flushed with nitrogen and 2,3-dimyristyloxypropylamine 5 (0.7 g, 1.5 mmol) was added. This was dissolved in anhydrous dichloromethane (15 ml), triethylamine was added (280 ul), and the reaction was left to stir at room temperature overnight. The solution was transferred to a separatory funnel with dichloromethane (5 ml) and washed with distilled water (2×20 ml). The organic layer was dried with magnesium sulfate and the dichloromethane was removed on the rotary evaporator. TLC (3% MeOH—CHCl$_3$, developed in Molybdate and iodine) showed that most of the starting material had reacted to form product. This resulting product was further purified by flash column chromatography (1.5-10% MeOH—CHCl$_3$) to yield 1.2 g (46.5%) of N-(2,3-dimyristyloxypropyl) carbamate PEG$_{2000}$ methyl ether 8.

9. Preparation of N-(2,3-dimyristyloxypropyl)succinamide PEG$_{2000}$ methyl ether (13)

For preparation of N-(2,3-dimyristyloxypropyl) succinamide PEG$_{2000}$ methyl ether (13), steps 1-5 described above were followed. The remaining procedure follows"

a. Preparation of PEG$_{2000}$ mesylate (9)

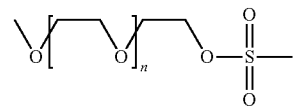

Mesyl anhydride (8.2 g, 47.1 mmol) was dissolved in anhydrous chloroform (80 ml). Pyridine (3.8 ml, 47.0 mmol) was added to the solution and fuming was observed while a white precipitate formed. A solution of PEG$_{2000}$ methyl ether (31.5 g, 15.5 mmol) in anhydrous chloroform (70 ml) was added and the reaction was left to stir for 3 hours. The white precipitate that had formed was filtered off and the chloroform solvent of the filtrate was removed on the rotary evaporator.

TLC (5% MeOH—CHCl₃, developed in iodine) indicated that most of the starting material had reacted to form product. This product was further purified by flash column chromatography (0-10% MeOH—CHCl₃) to yield 30.1 g (92.8%) of PEG$_{2000}$ mesylate 9 as a white solid.

b. Preparation of PEG$_{2000}$ phthalimide (10)

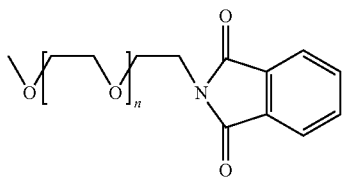

Potassium phthalimide (11.1 g, 59.7 mmol) was dissolved in anhydrous N,N-Dimethylformamide (400 ml). A solution of PEG$_{2000}$ mesylate 9 (35.0 g, 16.7 mmol) in anhydrous N,N-Dimethylformamide (100 ml) was added to the flask and the reaction was left to stir at 75° C. overnight. The N,N-Dimethylformamide solvent was removed on the rotary evaporator using a high vacuum pump instead of the usual aspirator. The resulting product was dissolved in dichloromethane (250 ml) and washed with distilled water (2×250 ml) and brine (250 ml). The dichloromethane solvent of the combined organic layers was removed on the rotary evaporator. TLC (7% MeOH—CHCl₃, visualized with UV light and Mary's Reagent) indicated that most of the starting material had reacted to form product. This resulting product was further purified by flash column chromatography (0-10% MeOH—CH₂Cl₂). The product was crystallized from ether to yield 19.4 g (54.1%) of the PEG$_{2000}$ phthalimide 10.

c. Preparation of PEG$_{2000}$ amine (11)

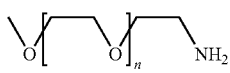

PEG$_{2000}$ phthalimide 10 (10.3 g, 4.8 mmol) was dissolved in ethanol (200 ml). Hydrazine monohydrate (6.0 ml, 123.7 mmol) was slowly added and the reaction was left to reflux at 100° C. overnight. The white precipitate was filtered off and the ethanol solvent was removed on the rotary evaporator. The resulting product was dissolved in chloroform and the remaining white solid that was insoluble in the chloroform was filtered off and again the chloroform was removed on the rotary evaporator. TLC (10% MeOH—CHCl₃, developed in iodine, Molybdate and Mary's Reagent) indicated that all the starting material had reacted to form product. This product was then crystallized from ether to yield 9.0 g (93.0%) of PEG$_{2000}$ amine 11 as a white powder.

d. Preparation of PEG$_{2000}$ succinamide (12)

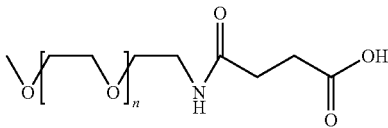

PEG$_{2000}$ amine 11 (9.0 g, 4.4 mmol) and succinic anhydride (3.8 g, 38.1 mmol) were dissolved in pyridine (100 ml) and the reaction was left to stir overnight. The pyridine solvent was removed on the rotary evaporator at 60° C. The residue was dissolved in distilled water (100 ml), acidified with hydrochloric acid, extracted with dichloromethane (100 ml, 2×70 ml), and dried with magnesium sulfate. TLC (10% MeOH—CHCl₃, developed in iodine) indicated that most of the starting material had reacted to form product. This product was further purified by flash column chromatography (0-10% MeOH—CHCl₃) to yield 5.2 g (55.9%) of PEG$_{2000}$ succinamide 12.

e. Preparation of N-(2,3-dimyristyloxypropyl) succinamide PEG$_{2000}$ methyl ether (13)

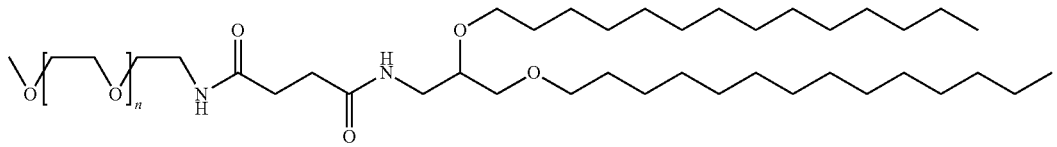

PEG$_{2000}$ succinamide (2.0 g, 0.9 mmol) and N-hydroxysuccinamide (0.2 g, 2.0 mmol) were dissolved in anhydrous chloroform (10 ml). Then, a solution of 1,3-Dicyclohexylcarbodiimide (0.3 g, 1.5 mmol) in anhydrous chloroform (5 ml) was added, and the reaction was left to stir for an hour. A solution of 1,2-dimyristyloxypropylamine 5 (0.48 g, 1.0 mmol) in anhydrous chloroform (5 ml) and triethylamine (0.6 ml, 4 mmol) was added and the reaction was left to stir for an hour. TLC (12% MeOH—CHCl₃, developed in Molybdate) indicated that most of the starting material had reacted to form product. The solution was filtered through Celite with dichloromethane, acidified with hydrochloric acid, and washed with distilled water (2×50 ml) and brine (50 ml). The aqueous layers were back extracted with dichloromethane (50 ml) and the combined organic layers were dried over magnesium sulfate. The product was further purified my flash column chromatography (0-7% MeOH—CHCl₃) to yield 1.8 g (69.0%) of N-(2,3-dimyristyloxypropyl) succinamide PEG$_{2000}$ methyl ether 13.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all Accession Nos., articles and references, including patent applications, patents and PCT publications, are incorporated herein by reference for all purposes.

What is claimed is:

1. A nucleic acid-lipid particle, said nucleic acid-lipid particle comprising:
   a chemically synthesized siRNA;
   a cationic lipid;
   a non-cationic lipid; and
   a conjugated lipid that inhibits aggregation of particles, wherein the conjugated lipid that inhibits aggregation of particles comprises a polyethyleneglycol-dialkyloxypropyl (PEG-DAA) conjugate having the following structure:

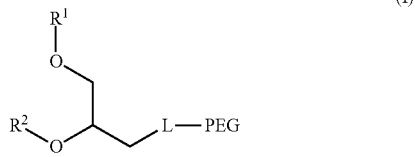

(I)

wherein:
R$^1$ and R$^2$ are independently selected and are alkyl groups having from about 10 to about 22 carbon atoms;
PEG is a polyethyleneglycol, wherein the terminal hydroxyl group is substituted with a methyl group; and
L is a carbamate linker moiety; and
wherein said siRNA is fully encapsulated in said nucleic acid-lipid particle.

2. The nucleic acid-lipid particle in accordance with claim 1, wherein said siRNA component of said nucleic acid-lipid particle is resistant in aqueous solution to degradation by a nuclease.

3. The nucleic acid-lipid particle in accordance with claim 1, wherein said particle has a median diameter of less than about 150 nm.

4. The nucleic acid-lipid particle in accordance with claim 1, wherein said siRNA comprises about 15 to about 60 nucleotides.

5. The nucleic acid-lipid particle in accordance with claim 1, wherein said cationic lipid is a member selected from the group consisting of N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxypropylamine (DODMA), and combinations thereof.

6. The nucleic acid-lipid particle in accordance with claim 1, wherein said non-cationic lipid is a member selected from the group consisting of dipalmitoylphosphatidylcholine (DPPC), dioleoylphosphatidylethanolamine (DOPE), palmitoyloleoylphosphatidylcholine (POPC), egg phosphatidylcholine (EPC), distearoylphosphatidylcholine (DSPC), cholesterol, and combinations thereof.

7. The nucleic acid-lipid particle in accordance with claim 1, wherein said cationic lipid comprises from about 2% to about 60% of the total lipid present in said particle.

8. The nucleic acid-lipid particle in accordance with claim 1, wherein said cationic lipid comprises from about 5% to about 45% of the total lipid present in said particle.

9. The nucleic acid-lipid particle in accordance with claim 1, wherein said cationic lipid comprises from about 40% to about 50% of the total lipid present in said particle.

10. The nucleic acid-lipid particle in accordance with claim 1, wherein said non-cationic lipid comprises from about 5% to about 90% of the total lipid present in said particle.

11. The nucleic acid-lipid particle in accordance with claim 1, wherein said non-cationic lipid comprises from about 20% to about 85% of the total lipid present in said particle.

12. The nucleic acid-lipid particle in accordance with claim 1, wherein said conjugated lipid that inhibits aggregation of particles comprises from about 0.5% to about 50% of the total lipid present in said particle.

13. The nucleic acid-lipid particle in accordance with claim 1, wherein said conjugated lipid that inhibits aggregation of particles comprises from about 0.5% to about 25% of the total lipid present in said particle.

14. The nucleic acid-lipid particle in accordance with claim 1, wherein said conjugated lipid that inhibits aggregation of particles comprises from about 1% to about 20% of the total lipid present in said particle.

15. The nucleic acid-lipid particle in accordance with claim 1, wherein said conjugated lipid that inhibits aggregation of particles comprises from about 3% to about 15% of the total lipid present in said particle.

16. The nucleic acid-lipid particle in accordance with claim 1, wherein said conjugated lipid that inhibits aggregation of particles comprises from about 4% to about 10% of the total lipid present in said particle.

17. The nucleic acid-lipid particle in accordance with claim 1, wherein said non-cationic lipid comprises dipalmitoylphosphatidylcholine (DPPC).

18. The nucleic acid-lipid particle in accordance with claim 1, wherein said nucleic acid-lipid particle further comprises cholesterol.

19. The nucleic acid-lipid particle in accordance with claim 18, wherein the cholesterol comprises from about 10% to about 60% of the total lipid present in said particle.

20. The nucleic acid-lipid particle in accordance with claim 18, wherein the cholesterol comprises from about 20% to about 45% of the total lipid present in said particle.

21. The nucleic acid-lipid particle in accordance with claim 1, wherein said particle has an siRNA:lipid ratio (mg:mg) of from about 0.01 to about 0.08.

22. The nucleic acid-lipid particle in accordance with claim 1, wherein said particle has an siRNA:lipid ratio (mg:mg) of about 0.04.

23. The nucleic acid-lipid particle in accordance with claim 1, wherein said particle has a median diameter of less than about 100 nm.

24. The nucleic acid-lipid particle in accordance with claim 1, wherein said non-cationic lipid comprises a phospholipid and cholesterol, and wherein R$^1$ and R$^2$ are both myristyl (C14).

25. The nucleic acid-lipid particle in accordance with claim 1, wherein said siRNA is about 15 to about 30 base pairs in length.

26. The nucleic acid-lipid particle in accordance with claim 1, wherein said siRNA is about 19 to about 25 base pairs in length.

27. The nucleic acid-lipid particle in accordance with claim 1, wherein said siRNA comprises 3' overhangs.

28. The nucleic acid-lipid particle in accordance with claim 1, wherein said siRNA comprises 2'-O-methyl ribonucleotides.

29. A pharmaceutical composition comprising a nucleic acid-lipid particle in accordance with claim 1 and a pharmaceutically acceptable carrier.

30. The nucleic acid-lipid particle in accordance with claim 1, wherein R$^1$ and R$^2$ are selected from the group consisting of lauryl (C12), myristyl (C14), palmityl (C16), stearyl (C18), and icosyl (C20).

31. The nucleic acid-lipid particle in accordance with claim 1, wherein R$^1$ and R$^2$ are the same.

32. The nucleic acid-lipid particle in accordance with claim 31, wherein R$^1$ and R$^2$ are both myristyl (C14).

33. The nucleic acid-lipid particle in accordance with claim 31, wherein R$^1$ and R$^2$ are both stearyl (C18).

34. The nucleic acid-lipid particle in accordance with claim 1, wherein said alkyl groups are saturated.

35. The nucleic acid-lipid particle in accordance with claim 1, wherein said alkyl groups are unsaturated.

36. The nucleic acid-lipid particle in accordance with claim 1, wherein said PEG has an average molecular weight of from about 550 daltons to about 8,500 daltons.

37. The nucleic acid-lipid particle in accordance with claim 1, wherein said PEG has an average molecular weight of from about 1,000 daltons to about 5,000 daltons.

38. The nucleic acid-lipid particle in accordance with claim 1, wherein said PEG has an average molecular weight of from about 1,000 daltons to about 3,000 daltons.

39. The nucleic acid-lipid particle in accordance with claim 1, wherein said PEG has an average molecular weight of about 2,000 daltons.

40. A method of introducing an siRNA into a cell, said method comprising contacting said cell with a nucleic acid-lipid particle in accordance with claim 1.

41. The method in accordance with claim 40, wherein the presence of said nucleic acid-lipid particle in said cell is detectable at least 24 hours after administration of said particle.

42. The method in accordance with claim 40, wherein the presence of said nucleic acid-lipid particle in said cell is detectable at least 48 hours after administration of said particle.

43. The method in accordance with claim 40, wherein said cell is in a mammal.

44. The method in accordance with claim 43, wherein more than 10% of said particles are present in the plasma of said mammal 24 hours after administration.

45. The method in accordance with claim 43, wherein the presence of said siRNA at a site distal to the site of administration is detectable for at least 48 hours after administration of said particle.

46. The method in accordance with claim 43, wherein the presence of said siRNA at a site distal to the site of administration is detectable for at least 24 hours after administration of said particle.

47. The method in accordance with claim 43, wherein the mammal is a human.

48. A method for silencing the expression of a target sequence, said method comprising administering to a mammalian subject a therapeutically effective amount of a nucleic acid-lipid particle in accordance with claim 1.

49. The method in accordance with claim 48, wherein said administration is intravenous.

50. The method in accordance with claim 48, wherein said mammalian subject is a human.

51. The method in accordance with claim 50, wherein said human has a disease or disorder associated with expression or overexpression of a gene comprising a target sequence for said siRNA.

52. The method in accordance with claim 51, wherein said gene is selected from the group consisting of a gene associated with viral infection and survival, a gene associated with a metabolic disease or disorder, and a gene associated with tumorigenesis and cell transformation.

53. A method for the in vivo delivery of an siRNA, said method comprising administering to a mammalian subject a nucleic acid-lipid particle in accordance with claim 1.

54. The method in accordance with claim 53, wherein said administration is intravenous.

55. The method in accordance with claim 53, wherein said mammalian subject is a human.

56. The method in accordance with claim 55, wherein said human has a disease or disorder associated with expression or overexpression of a gene comprising a target sequence for said siRNA.

57. The method in accordance with claim 56, wherein said gene is selected from the group consisting of a gene associated with viral infection and survival, a gene associated with a metabolic disease or disorder, and a gene associated with tumorigenesis and cell transformation.

58. A method for the in vivo delivery of an siRNA to a liver cell, said method comprising administering to a mammalian subject a nucleic acid-lipid particle in accordance with claim 1.

59. The method in accordance with claim 58, wherein said administration is intravenous.

60. The method in accordance with claim 58, wherein said mammalian subject is a human.

61. The method in accordance with claim 60, wherein said human has a disease or disorder associated with expression or overexpression of a gene comprising a target sequence for said siRNA.

62. The method in accordance with claim 61, wherein said gene is associated with a metabolic disease or disorder.

63. The method in accordance with claim 62, wherein said metabolic disease or disorder is a dyslipidemia.

* * * * *